United States Patent
Soni et al.

(10) Patent No.: US 11,984,201 B2
(45) Date of Patent: May 14, 2024

(54) MEDICAL MACHINE SYNTHETIC DATA AND CORRESPONDING EVENT GENERATION

(71) Applicant: GE Precision Healthcare LLC, Wauwatosa, WI (US)

(72) Inventors: Ravi Soni, San Ramon, CA (US); Min Zhang, San Ramon, CA (US); Gopal B. Avinash, San Ramon, CA (US); Venkata Ratnam Saripalli, San Ramon, CA (US); Jiahui Guan, San Ramon, CA (US); Dibyajyoti Pati, San Ramon, CA (US); Zili Ma, San Ramon, CA (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 583 days.

(21) Appl. No.: 16/689,798

(22) Filed: Nov. 20, 2019

(65) Prior Publication Data
US 2020/0342362 A1    Oct. 29, 2020

Related U.S. Application Data

(60) Provisional application No. 62/838,022, filed on Apr. 24, 2019.

(51) Int. Cl.
*G16H 10/00* (2018.01)
*A61B 5/00* (2006.01)
(Continued)

(52) U.S. Cl.
CPC .......... *G16H 10/00* (2018.01); *A61B 5/7267* (2013.01); *G06F 9/451* (2018.02); *G06N 3/044* (2023.01);
(Continued)

(58) Field of Classification Search
CPC ........ G16H 10/00; G16H 40/67; G16H 50/30; G06H 15/00; G06F 9/451; G06N 20/20;
(Continued)

(56) References Cited

U.S. PATENT DOCUMENTS

| 9,053,222 B2 | 6/2015 | Lynn et al. |
| 10,490,309 B1 | 11/2019 | McNair |

(Continued)

FOREIGN PATENT DOCUMENTS

| CN | 104866727 A | 8/2015 |
| CN | 107615395 A | 1/2018 |

(Continued)

OTHER PUBLICATIONS

Shoham et al., The AI Index 2018, Annual Report. In AI Index Steering Committee Human-Centered AI Initiative, Stanford, University, Stanford, CA, Dec. 2018, 94 pages.
(Continued)

*Primary Examiner* — Hai Tao Sun
(74) *Attorney, Agent, or Firm* — Hanley, Flight & Zimmerman, LLC

(57) ABSTRACT

Systems, apparatus, instructions, and methods for medical machine time-series event data generation are disclosed. An example synthetic time series data generation apparatus is to generate a synthetic data set including multi-channel time-series data and associated annotation using a first artificial intelligence network model. The example apparatus is to analyze the synthetic data set with respect to a real data set using a second artificial intelligence network model. When the second artificial intelligence network model classifies the synthetic data set as a first classification, the example apparatus is to adjust the first artificial intelligence network model using feedback from the second artificial intelligence network model. When the second artificial intelligence net-
(Continued)

work model classifies the synthetic data set as a second classification, the example apparatus is to output the synthetic data set.

14 Claims, 17 Drawing Sheets

(51) Int. Cl.
*G06F 9/451* (2018.01)
*G06N 3/044* (2023.01)
*G06N 3/08* (2023.01)
*G06N 20/00* (2019.01)
*G06N 20/20* (2019.01)
*G16H 10/60* (2018.01)
*G16H 15/00* (2018.01)
*G16H 40/67* (2018.01)
*G16H 50/30* (2018.01)

(52) U.S. Cl.
CPC .............. *G06N 3/08* (2013.01); *G06N 20/00* (2019.01); *G06N 20/20* (2019.01); *G16H 10/60* (2018.01); *G16H 15/00* (2018.01); *G16H 40/67* (2018.01); *G16H 50/30* (2018.01); *A61B 5/7275* (2013.01); *G06T 2207/20081* (2013.01); *G06T 2207/20084* (2013.01)

(58) Field of Classification Search
CPC ........ G06N 20/00; G06N 3/0445; G06N 3/08; A61B 5/7267
USPC .......................................................... 706/45
See application file for complete search history.

(56) References Cited

U.S. PATENT DOCUMENTS

| | | | |
|---|---|---|---|
| 10,650,306 B1* | 5/2020 | Kumar | G06N 3/0472 |
| 10,766,137 B1* | 9/2020 | Porter | G06N 3/04 |
| 11,404,145 B2* | 8/2022 | Saripalli | A61B 5/7267 |
| 2005/0119534 A1 | 6/2005 | Trost et al. | |
| 2015/0112182 A1* | 4/2015 | Sharma | A61B 6/032 |
| | | | 600/408 |
| 2016/0135706 A1 | 5/2016 | Sullivan et al. | |
| 2017/0032243 A1 | 2/2017 | Corrado et al. | |
| 2018/0107791 A1 | 4/2018 | Guo et al. | |
| 2018/0122506 A1 | 5/2018 | Grantcharov et al. | |
| 2018/0137941 A1 | 5/2018 | Chen | |
| 2018/0144214 A1 | 5/2018 | Hsieh et al. | |
| 2018/0315182 A1* | 11/2018 | Rapaka | G06V 10/7747 |
| 2019/0034591 A1 | 1/2019 | Mossin et al. | |
| 2019/0035075 A1* | 1/2019 | Middlebrooks | G06T 7/0012 |
| 2019/0198156 A1* | 6/2019 | Madani | G06N 3/08 |
| 2019/0286990 A1 | 9/2019 | Kenney et al. | |
| 2019/0325597 A1* | 10/2019 | Chakravarty | G06T 7/74 |
| 2019/0362846 A1 | 11/2019 | Vodencarevic | |
| 2019/0371475 A1 | 12/2019 | Oliveira et al. | |
| 2019/0374160 A1 | 12/2019 | Yin et al. | |
| 2020/0176117 A1 | 6/2020 | Lee | |
| 2020/0185102 A1 | 6/2020 | Leventhal et al. | |
| 2020/0244969 A1* | 7/2020 | Bhorkar | H04N 19/147 |
| 2020/0327456 A1 | 10/2020 | Sathe et al. | |
| 2020/0327986 A1 | 10/2020 | Kurniawan et al. | |
| 2021/0019863 A1* | 1/2021 | Kaethner | G06T 5/002 |
| 2021/0056413 A1 | 2/2021 | Cheung | |
| 2021/0076966 A1 | 3/2021 | Grantcharov et al. | |

FOREIGN PATENT DOCUMENTS

| | | |
|---|---|---|
| CN | 107909621 A | 4/2018 |
| CN | 108309263 A | 7/2018 |
| CN | 108491497 A | 9/2018 |
| CN | 109376862 A | 2/2019 |
| CN | 109378064 A | 2/2019 |
| CN | 109522973 A | 3/2019 |
| KR | 101848321 B1 | 4/2018 |
| KR | 101843066 B1 | 5/2018 |
| WO | 2013036677 A1 | 3/2013 |

OTHER PUBLICATIONS

Abadi et al., TensorFlow: Large-Scale Machine Learning on Heterogeneous Systems. https://www.tensorflow.org, Nov. 9, 2015, 19 pages.

Yangqing Jia et al., Caffe: Convolutional architecture for fast feature embedding. In Proceedings of the ACM International Conference on Multimedia, MM '14, Orlando, FL, USA, Nov. 3-7, 2014, 4 pages.

Tianqi Chen et al., MXNet: A Flexible and Efficient Machine Learning Library for Heterogeneous Distributed Systems. In Neural Information Processing Systems, Workshop on Machine Learning Systems, 2015, 6 pages.

Frank Seide et al., CNTK: Microsoft's Open-Source Deep-Learning Toolkit. In KDD. Association for Computing Machinery, 2016, 5 pages. Abstract only.

Adam Paszke et al.,Automatic Differentiation in PyTorch. In NIPS Autodiff Workshop, 2017, 4 pages.

Francois Chollet et al., Keras. https://keras.io, 2015, 5 pages.

Jeremy Howard et al,. Fastai:. https://github.com/fastai/fastai, last retrieved on Apr. 27, 2020, 6 pages.

Piero Molino et al., Ludwig: a type-based declarative deep learning toolbox, 2019, 15 pages.

McInnes et al., UMAP: Uniform Manifold Approximation and Projection for Dimension Reduction. ArXiv e-prints, 2018, 51 pages.

Karen Simonyan et al., Deep Inside Convolutional Networks: Visualising Image Classification Models and Saliency Maps. In 2nd International Conference on Learning Representations, ICLR 2014, Banff, AB, Canada, Apr. 14-16, 2014, Workshop Track Proceedings, 8 pages.

Mukund Sundararajan et al., Axiomatic Attribution for Deep Networks. In Proceedings of the 34th International Conference on Machine Learning, ICML 2017, Sydney, NSW, Australia, Aug. 6-11, 2017, 11 pages.

Chris Olah et al., Feature Visualization. https://distill.pub/2017/feature visualization, Nov. 7, 2017, 9 Pages.

Bee Lim et al., Enhanced Deep Residual Networks for Single Image Super-Resolution. In 2017 IEEE Conference on Computer Vision and Pattern Recognition Workshops, CVPR Workshops 2017, Honolulu, HI, USA, Jul. 21-26, 2017, 9 pages.

Tero Karras et al., Progressive Growing of GANs for Improved Quality, Stability, and Variation. In 6th International Conference on Learning Representations, ICLR 2018, Vancouver, BC, Canada, Apr. 30-May 3, 2018, Conference Track Proceedings, 26 pages.

Ian J. Goodfellow et al., Explaining and Harnessing Adversarial Examples. In 3rd International Conference on Learning Representations, ICLR 2015, San Diego, CA, USA, May 7-9, 2015, Conference Track Proceedings, 11 pages.

Alec Radford et al., Unsupervised Representation Learning with Deep Convolutional Generative Adversarial Networks. In 4th International Conference on Learning Representations, ICLR 2016, San Juan, Puerto Rico, May 2-4, 2016, Conference Track Proceedings, 16 pages.

Jun-Yan Zhu et al., Unpaired Image-to-Image Translation using Cycle Consistent Adversarial Networks. In 2017 IEEE International Conference on Computer Vision (ICCV), 10 pages.

Greg Brockman et al., OpenAI Gym, 2016, 4 pages.

Sutton et al., A. G. Introduction to reinforcement. Complete Draft Nov. 5, 2017, 445 pages.

Mahmud et al., Applications of Deep Learning and Reinforcement Learning to Biological Data, IEEE Trans. Neural Netw. Learn. Syst., 2018, doi: 10.1109/TNNLS.2018.2790388, 33 pages.

Topol, "High-performance medicine: the convergence of human and artificial intelligence", https://www.nature.com/articles/s41591-018-0300-7,last retrieved on Apr. 27, 2020, 13 pages.

(56) References Cited

OTHER PUBLICATIONS

Niranjani Prasad et al., A Reinforcement Learning Approach to Weaning of Mechanical Ventilation in Intensive Care Units, 2017, 10 pages.
Pablo Escandell-Montero et al., Optimization of anemia treatment in hemodialysis patients via reinforcement learning. Artificial Intelligence in Medicine, 62(1):47-60, 2014. ISSN 0933-3657, 17 pages.
Nemati et al., Optimal medication dosing from suboptimal clinical examples: A deep reinforcement learning approach. In 2016 38th Annual International Conference of the IEEE Engineering in Medicine and Biology Society (EMBC), pp. 2978-2981, Aug. 2016, Abstract only.
Padmanabhan et al., Closed-loop control of anesthesia and mean arterial pressure using reinforcement learning. In 2014 IEEE Symposium on Adaptive Dynamic Programming and Reinforcement Learning (ADPRL), pp. 1-8, Dec. 2014, 11 pages.
Martina Mueller et al., Can machine learning methods predict extubation outcome in premature infants as well as clinicians? Journal of neonatal biology, 2013, 18 pages.
Hung-Ju Kuo et al., Improvement in the prediction of ventilator weaning outcomes by an artificial neural network in a medical icu. Respiratory care, 60(11):1560-1569, 2015, 10 pages.
Yuanyuan Gao et al., Incorporating association rule networks in feature category-weighted naive bayes model to support weaning decision making. Decision Support Systems, 2017, Abstract only.
Hyung-Chul et al., Vital Recorder-a free research tool for automatic recording of high-resolution time-synchronised physiological data from multiple anaesthesia devices. Sci Rep. 2018, 8 pages.
Samudra et al., Scheduling operating rooms: achievements, challenges and pitfalls, 2016, 42 pages.
Li-Fang Cheng et al., Sparse Multi-Output Gaussian Processes for Medical Time Se-ries Prediction. ArXiv e-prints, Mar. 2017, 62 pages.
Brunton et al., "Extracting Spatial-Temporal Coherent Patterns in Large-Scale Neural Recordings Using Dynamic Mode Decomposition," Journal of Neuroscience Methods, vol. 258, Jan. 2016, Abstract only.
Joshua L Proctor et al., Dynamic mode decomposition with control. SIAM Journal on Applied Dynamical Systems, 15(1):142-161, 2016, 20 pages.
Omer Gottesman et al., Evaluating reinforcement learning algorithms in observational health settings. CoRR,abs/1805.12298, 2018, 16 pages.
Lina Zhou et al., Machine learning on big data: Opportunities and challenges. Neurocomputing, 237:350-361, 2017, Abstract only.
Cao Xiao et al., Opportunities and challenges in developing deep learning models using electronic health records data: a systematic review. In JAMIA, 2018, 10 pages.
Marzyeh Ghassemi et al., Opportunities in machine learning for healthcare, 2018, 10 pages.
Andre Esteva et al., A guide to deep learning in healthcare. Nature medicine, 2019, 7 pages.
Xing Wang et al., A machine learning approach to false alarm detection for critical arrhythmia alarms. In 2015 IEEE 14th international conference on machine learning and applications (ICMLA), pp. 202-207. IEEE, 2015, Abstract only.
Patrick Schwab et al., Not to cry wolf: Distantly supervised multitask learning in critical care, 2018, 14 pages.
Richard S Sutton et al., Introduction to reinforcement learning, vol. 2. MIT press Cambridge, 1998, 352 pages.
Mnih Volodymyr et al., Human-level control through deep reinforcement learning, 2015, 13 pages.

Omid Sayadi et al., Life-threatening arrhythmia verification in icu patients using the joint cardiovascular dynamical model and a bayesian filter. IEEE Transactions on Biomedical Engineering, 2011, 10 pages.
Rebeca Salas-Boni et al., False ventricular tachycardia alarm suppression in the icu based on the discrete wavelet transform in the ecg signal. Journal of electrocardiology, 2014, Abstract only.
Joachim Behar et al., Ecg signal quality during arrhythmia and its application to false alarm reduction. IEEE transactions on biomedical engineering, 60 (6):1660-1666, 2013, 8 pages.
Gari D Clifford et al., The physionet/computing in cardiology challenge 2015: reducing false arrhythmia alarms in the icu. In 2015 Computing in Cardiology Conference (CinC), pp. 273-276. IEEE, 2015, 8 pages.
Plesinger et al., Taming of the monitors: reducing false alarms in intensive care units. Physiological measurement, 2016, Abstract only.
Volodymyr et al., Asynchronous methods for deep reinforcement learning. In International conference on machine learning, pp. 1928-1937, 2016, 19 pages.
Leo Kobayashi et al., Development and deployment of an open, modular, near-real-time patient monitor datastream conduit toolkit to enable healthcare multimodal data fusion in a live emergency department setting for experimental bedside clinical informatics research. IEEE Sensors Letters, 3(1):1-4, 2018, Abstract only, 2 pages.
Acharya et al., "Deep convolutional neural network for the automated detection and diagnosis of seizure using EEG signals," Computers in Biology and Medicine 100 (2018) 270-278, 9 pages.
Johnson et al., "Machine Learning and Decision Support in Critical Care," Proceedings of the IEEE, vol. 104, No. 2, Feb. 2016, 23 pages.
GE, "Hospital leverages Carestation Insights to reduce average fresh gas flow rates," 2017, 2 pages.
Baytas et al., "Patient Subtyping via Time-Aware LSTM Networks," 2017 research Paper, 10 pages.
Chul Lee et al., "Vital Recorder—a free research tool for automatic recording of high-resolution time-synchronised physiological data from multiple anaesthesia devices," 2018, 8 pages.
Benaich et al., "State of AI Report," Jun. 28, 2019, 136 pages.
Slachta, "Deep learning ECG analysis facilitates screening for hyperkalemia," Apr. 10, 2019, 3 pages.
Faust et al., "Deep learning for healthcare applications based on physiological signals: A review," http://www.elsevier.com/locate/cmpb, 2018, 13 pages.
Luo et al., "Multivariate Time Series Imputation with Generative Adversarial Networks," 32nd Conference on Neural Information Processing Systems (NeurIPS 2018), Montréal, Canada, 12 pages.
1 KR application 10-2020-0047083 filed Apr. 19, 2020—Office Action issued May 19, 2022; 6 pages.
Soni, "Supervised vs. Unsupervised Learning," towards data science, https://towardsdatascience.com/supervised-vs-unsupervised-learning-14f68e32ea8d Mar. 22, 2018, 11 pages.
Ferguson, "Why It's Important to Standardize Your Data," humans of data, https://humansofdata.atlan.com/2018/12/data-standardization/ Dec. 10, 2018, 9 pages.
Korean Intellectual Property Office, "Written Decision on Registration," issued in connection with Korean Patent Application No. 10-2020-0047083, dated Nov. 23, 2022, 6 pages. [English Translation Included].
China National Intellectual Property Administration, "First Search," issued in connection with Chinese Patent Application No. 2020103245650, dated Sep. 14, 2023, 4 pages.

\* cited by examiner

MEDICAL MACHINE SYNTHETIC DATA AND CORRESPONDING EVENT GENERATION

CROSS-REFERENCE TO RELATED APPLICATIONS

This patent arises from U.S. Provisional Patent Application Ser. No. 62/838,022, which was filed on Apr. 24, 2019. U.S. Provisional Patent Application Ser. No. 62/838,022 is hereby incorporated herein by reference in its entirety. Priority to U.S. Provisional Patent Application Ser. No. 62/838,022 is hereby claimed.

FIELD OF THE DISCLOSURE

This disclosure relates generally to synthetic data and, more particularly, to generation of medical machine synthetic data and corresponding events.

BACKGROUND

The statements in this section merely provide background information related to the disclosure and may not constitute prior art.

Healthcare environments, such as hospitals or clinics, include information systems, such as hospital information systems (HIS), radiology information systems (RIS), clinical information systems (CIS), and cardiovascular information systems (CVIS), and storage systems, such as picture archiving and communication systems (PACS), library information systems (LIS), and electronic medical records (EMR). Information stored can include patient medication orders, medical histories, imaging data, test results, diagnosis information, management information, and/or scheduling information, for example. A wealth of information is available, but the information can be siloed in various separate systems requiring separate access, search, and retrieval. Correlations between healthcare data remain elusive due to technological limitations on the associated systems.

Further, healthcare provider consolidations create geographically distributed hospital networks in which physical contact with systems is too costly. At the same time, referring physicians want more direct access to supporting data in reports along with better channels for collaboration. Physicians have more patients, less time, and are inundated with huge amounts of data, and they are eager for assistance. However, large datasets are necessary for computer-driven solutions, such as neural networks and other "artificial intelligence" to assist human clinicians with analysis, optimization, improvement, and/or other decision support. Such large datasets are often missing or unobtainable with current systems and restrictions.

BRIEF DESCRIPTION

Systems, apparatus, instructions, and methods for medical machine time-series event data generation are disclosed.

Certain examples provide a synthetic time series data generation apparatus. The example apparatus includes memory storing instructions; and at least one processor to execute the instructions. The example processor is to at least generate a synthetic data set including multi-channel time-series data and associated annotation using a first artificial intelligence network model; and analyze the synthetic data set with respect to a real data set using a second artificial intelligence network model. When the second artificial intelligence network model classifies the synthetic data set as a first classification, the example processor is to adjust the first artificial intelligence network model using feedback from the second artificial intelligence network model. When the second artificial intelligence network model classifies the synthetic data set as a second classification, the example processor is to output the synthetic data set.

Certain examples provide at least one tangible computer-readable storage medium including instructions that, when executed, cause at least one processor to at least: generate a synthetic data set including multi-channel time-series data and associated annotation using a first artificial intelligence network model; analyze the synthetic data set with respect to a real data set using a second artificial intelligence network model; when the second artificial intelligence network model classifies the synthetic data set as a first classification, adjust the first artificial intelligence network model using feedback from the second artificial intelligence network model; and when the second artificial intelligence network model classifies the synthetic data set as a second classification, output the synthetic data set.

Certain examples provide a computer-implemented method to generate synthetic time series data and associated annotation. The example method includes: generating, using at least one processor, a synthetic data set including multi-channel time-series data and associated annotation using a first artificial intelligence network model. The example method includes analyzing, using the at least one processor, the synthetic data set with respect to a real data set using a second artificial intelligence network model. The example method includes, when the second artificial intelligence network model classifies the synthetic data set as a first classification, adjusting, using the at least one processor, the first artificial intelligence network model using feedback from the second artificial intelligence network model. The example method includes, when the second artificial intelligence network model classifies the synthetic data set as a second classification, outputting, using the at least one processor, the synthetic data set.

DETAILED DESCRIPTION OF CERTAIN EMBODIMENTS

Figure 1:
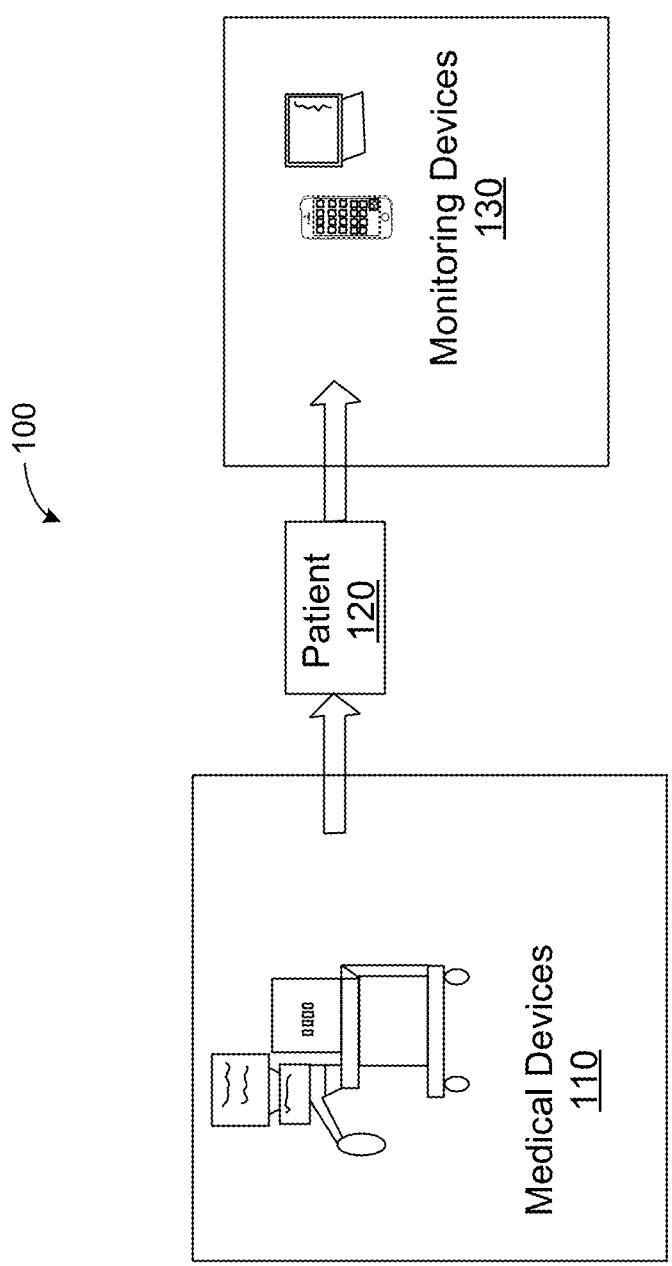
FIG. 1 is a block diagram of an example system including medical devices and associated monitoring devices for a patient.

In the following detailed description, reference is made to the accompanying drawings that form a part hereof, and in which is shown by way of illustration specific examples that may be practiced. These examples are described in sufficient detail to enable one skilled in the art to practice the subject matter, and it is to be understood that other examples may be utilized and that logical, mechanical, electrical and other changes may be made without departing from the scope of the subject matter of this disclosure. The following detailed description is, therefore, provided to describe an exemplary implementation and not to be taken as limiting on the scope of the subject matter described in this disclosure. Certain features from different aspects of the following description may be combined to form yet new aspects of the subject matter discussed below.

When introducing elements of various embodiments of the present disclosure, the articles "a," "an," "the," and "said" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object.

As used herein, the terms "system," "unit," "module," "engine," etc., may include a hardware and/or software system that operates to perform one or more functions. For example, a module, unit, or system may include a computer processor, controller, and/or other logic-based device that performs operations based on instructions stored on a tangible and non-transitory computer readable storage medium, such as a computer memory. Alternatively, a module, unit, engine, or system may include a hard-wired device that performs operations based on hard-wired logic of the device. Various modules, units, engines, and/or systems shown in the attached figures may represent the hardware that operates based on software or hardwired instructions, the software that directs hardware to perform the operations, or a combination thereof.

As used herein, singular references (e.g., "a", "an", "first", "second", etc.) do not exclude a plurality. The term "a" or "an" entity, as used herein, refers to one or more of that entity. The terms "a" (or "an"), "one or more", and "at least one" can be used interchangeably herein. Furthermore, although individually listed, a plurality of means, elements or method actions may be implemented by, e.g., a single unit or processor. Additionally, although individual features may be included in different examples or claims, these may possibly be combined, and the inclusion in different examples or claims does not imply that a combination of features is not feasible and/or advantageous.

The term "and/or" when used, for example, in a form such as A, B, and/or C refers to any combination or subset of A, B, C such as (1) A alone, (2) B alone, (3) C alone, (4) A with B, (5) A with C, (6) B with C, and (7) A with B and with C. As used herein in the context of describing structures, components, items, objects, and/or things, the phrase "at least one of A and B" is intended to refer to implementations including any of (1) at least one A, (2) at least one B, and (3) at least one A and at least one B. Similarly, as used herein in the context of describing structures, components, items, objects and/or things, the phrase "at least one of A or B" is intended to refer to implementations including any of (1) at least one A, (2) at least one B, and (3) at least one A and at least one B. As used herein in the context of describing the performance or execution of processes, instructions, actions, activities and/or steps, the phrase "at least one of A and B" is intended to refer to implementations including any of (1) at least one A, (2) at least one B, and (3) at least one A and at least one B. Similarly, as used herein in the context of describing the performance or execution of processes, instructions, actions, activities, and/or steps, the phrase "at least one of A or B" is intended to refer to implementations including any of (1) at least one A, (2) at least one B, and (3) at least one A and at least one B.

In addition, it should be understood that references to "one embodiment" or "an embodiment" of the present disclosure are not intended to be interpreted as excluding the existence of additional embodiments that also incorporate the recited features.

Machine and patient physiological signals can be combined to improve detection, prediction, and classification of events occurring during a medical procedure, health monitoring, other patient care, etc. In certain examples disclosed herein, data-driven generation of such events helps to lower healthcare costs and improve quality of care by using synthetic data/events for data augmentation, imputation of missing data, etc. Certain examples provide deep generative models to generate synthetic data and corresponding events.

An example framework includes a computer and/or other processor executing one or more deep generative models such as a Generative Adversarial Network, etc., trained on aggregated medical machine time series data converted into a single standardized data structure format. The data can be organized in an ordered arrangement per patient to generate synthetic data samples and corresponding synthetic events and/or to generate missing data for time-series real data imputation, for example. Thus, additional, synthetic data/events can be generated to provide more data for training, testing, etc., of artificial intelligence network models, and/or data missing from a time series can be imputed and/or otherwise interpolated to provide a time series of data for modeling, analysis, etc.

For example, sensor data in a time series waveform can suffer from errors or other deficiencies due to signal interference, communication issues, and/or other data loss resulting in gaps or missing data in the waveform. Certain examples determine replacement data to fill in or complete the waveform so that an artificial intelligence model, which may be expecting a complete waveform to process to a conclusion, receives a complete waveform for processing. As such, while gaps in the time series data may otherwise cause an artificial intelligence model to "break" and return no result, an improper/incorrect result, etc., certain examples identify and fill in the gaps in the time series data to allow the artificial intelligence model to process the input data set.

Medical data can be obtained from imaging devices, sensors, laboratory tests, and/or other data sources. Alone or in combination, medical data can assist in diagnosing a patient, treating a patient, forming a profile for a patient population, influencing a clinical protocol, etc. However, to be useful, medical data must be organized properly for analysis and correlation beyond a human's ability to track and reason. Computers and associated software and data constructs can be implemented to transform disparate medical data into actionable results.

For example, imaging devices (e.g., gamma camera, positron emission tomography (PET) scanner, computed tomography (CT) scanner, X-Ray machine, magnetic resonance (MR) imaging machine, ultrasound scanner, etc.) generate two-dimensional (2D) and/or three-dimensional (3D) medical images (e.g., native Digital Imaging and Communications in Medicine (DICOM) images) representative of the parts of the body (e.g., organs, tissues, etc.) to diagnose and/or treat diseases. Other devices such as electrocardiogram (ECG) systems, echoencephalograph (EEG), pulse oximetry (SpO2) sensors, blood pressure measuring cuffs, etc., provide one-dimensional waveform and/or time series data regarding a patient.

Acquisition, processing, analysis, and storage of time-series data (e.g., one-dimensional waveform data, etc.) obtained from one or more medical machines and/or devices play an important role in diagnosis and treatment of patients in a healthcare environment. Devices involved in the workflow can be configured, monitored, and updated throughout operation of the medical workflow. Machine learning can be used to help configure, monitor, and update the medical workflow and devices.

Machine learning techniques, whether deep learning networks or other experiential/observational learning system, can be used to characterize and otherwise interpret, extrapolate, conclude, and/or complete acquired medical data from a patient, for example. Deep learning is a subset of machine learning that uses a set of algorithms to model high-level abstractions in data using a deep graph with multiple processing layers including linear and non-linear transformations. While many machine learning systems are seeded with initial features and/or network weights to be modified through learning and updating of the machine learning network, a deep learning network trains itself to identify "good" features for analysis. Using a multilayered architecture, machines employing deep learning techniques can process raw data better than machines using conventional machine learning techniques. Examining data for groups of highly correlated values or distinctive themes is facilitated using different layers of evaluation or abstraction.

Throughout the specification and claims, the following terms take the meanings explicitly associated herein, unless the context clearly dictates otherwise. The term "deep learning" is a machine learning technique that utilizes multiple data processing layers to recognize various structures in data sets and classify the data sets with high accuracy. A deep learning network (DLN), also referred to as a deep neural network (DNN), can be a training network (e.g., a training network model or device) that learns patterns based on a plurality of inputs and outputs. A deep learning network/deep neural network can be a deployed network (e.g., a deployed network model or device) that is generated from the training network and provides an output in response to an input.

The term "supervised learning" is a deep learning training method in which the machine is provided already classified data from human sources. The term "unsupervised learning" is a deep learning training method in which the machine is not given already classified data but makes the machine useful for abnormality detection. The term "semi-supervised learning" is a deep learning training method in which the machine is provided a small amount of classified data from human sources compared to a larger amount of unclassified data available to the machine.

The term "convolutional neural networks" or "CNNs" are biologically inspired networks of interconnected data used in deep learning for detection, segmentation, and recognition of pertinent objects and regions in datasets. CNNs evaluate raw data in the form of multiple arrays, breaking the data in a series of stages, examining the data for learned features.

The term "transfer learning" is a process of a machine storing the information used in properly or improperly solving one problem to solve another problem of the same or similar nature as the first. Transfer learning may also be known as "inductive learning". Transfer learning can make use of data from previous tasks, for example.

The term "active learning" is a process of machine learning in which the machine selects a set of examples for which to receive training data, rather than passively receiving examples chosen by an external entity. For example, as a machine learns, the machine can be allowed to select examples that the machine determines will be most helpful for learning, rather than relying only an external human expert or external system to identify and provide examples.

The term "computer aided detection" or "computer aided diagnosis" refer to computers that analyze medical data to suggest a possible diagnosis.

Deep learning is a class of machine learning techniques employing representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms. While machine learning, for example, involves an identification of features to be used in training the network, deep learning processes raw data to identify features of interest without the external identification.

Deep learning in a neural network environment includes numerous interconnected nodes referred to as neurons. Input neurons, activated from an outside source, activate other neurons based on connections to those other neurons which are governed by the machine parameters. A neural network behaves in a certain manner based on its own parameters. Learning refines the machine parameters, and, by extension, the connections between neurons in the network, such that the neural network behaves in a desired manner.

A variety of artificial intelligence networks can be deployed to process input data. For example, deep learning that utilizes a convolutional neural network segments data using convolutional filters to locate and identify learned, observable features in the data. Each filter or layer of the CNN architecture transforms the input data to increase the selectivity and invariance of the data. This abstraction of the data allows the machine to focus on the features in the data it is attempting to classify and ignore irrelevant background information.

Deep learning operates on the understanding that many datasets include high level features which include low level features. While examining an image, for example, rather than looking for an object, it is more efficient to look for edges which form motifs which form parts, which form the object being sought. These hierarchies of features can be found in many different forms of data such as speech and text, etc.

Learned observable features include objects and quantifiable regularities learned by the machine during supervised learning. A machine provided with a large set of well classified data is better equipped to distinguish and extract the features pertinent to successful classification of new data.

A deep learning machine that utilizes transfer learning may properly connect data features to certain classifications affirmed by a human expert. Conversely, the same machine can, when informed of an incorrect classification by a human expert, update the parameters for classification. Settings and/or other configuration information, for example, can be guided by learned use of settings and/or other configuration information, and, as a system is used more (e.g., repeatedly and/or by multiple users), a number of variations and/or other possibilities for settings and/or other configuration information can be reduced for a given situation.

An example deep learning neural network can be trained on a set of expert classified data, for example. This set of data builds the first parameters for the neural network, and this would be the stage of supervised learning. During the stage of supervised learning, the neural network can be tested whether the desired behavior has been achieved.

Once a desired neural network behavior has been achieved (e.g., a machine has been trained to operate according to a specified threshold, etc.), the machine can be deployed for use (e.g., testing the machine with "real" data, etc.). During operation, neural network classifications can be confirmed or denied (e.g., by an expert user, expert system, reference database, etc.) to continue to improve neural network behavior. The example neural network is then in a state of transfer learning, as parameters for classification that determine neural network behavior are updated based on ongoing interactions. In certain examples, the neural network can provide direct feedback to another process. In certain examples, the neural network outputs data that is buffered (e.g., via the cloud, etc.) and validated before it is provided to another process.

Deep learning machines can utilize transfer learning when interacting with physicians to counteract the small dataset available in the supervised training. These deep learning machines can improve their computer aided diagnosis over time through training and transfer learning. However, a larger dataset results in a more accurate, more robust deployed deep neural network model that can be applied to transform disparate medical data into actionable results (e.g., system configuration/settings, computer-aided diagnosis results, image enhancement, etc.).

Certain examples provide a framework including a) a computer executing one or more deep learning (DL) models and hybrid deep reinforcement learning (RL) models trained on aggregated machine timeseries data converted into the single standardized data structure format and in an ordered arrangement per patient to predict one or more future events and summarize pertinent past machine events related to the predicted one or more future machine events on a consistent input time series data of a patient having the standardized data structure format; and b) a healthcare provider-facing interface of an electronic device for use by a healthcare provider treating the patient configured to display the predicted one or more future machine events and the pertinent past machine events of the patient.

In certain examples, machine signals, patient physiological signals, and a combination of machine and patient physiological signals provide improved prediction, detection, and/or classification of events during a medical procedure. The three data contexts are represented in Table 1 below, associated with example artificial intelligence models that can provide a prediction, detection, and/or classification using the respective data source. Data-driven predictions of events related to a medical treatment/procedure help to lower healthcare costs and improve the quality of care. Certain examples involve DL models, hybrid RL models, and DL+Hybrid RL combination models for prediction of such events. Similarly, data-driven detection and classification of events related to a patient and/or machine helps to lower healthcare costs and improve the quality of care. Certain examples involve DL models, hybrid RL models, and DL+Hybrid RL combination models for detection and classification of such events.

As shown below, machine data, patient monitoring data, and a combination of machine and monitoring data can be used with one or more artificial intelligence constructs to form one or more predictions, detections, and/or classifications, for example.

TABLE 1

Data source and associated prediction, detection, and/or classification model examples.

| Data Source | Prediction/Detection/Classification |
| --- | --- |
| Machine Data | DL |
| | Hybrid RL |
| | DL + Hybrid RL |
| Monitoring (Patient data) | DL |
| | Hybrid RL |
| | DL + Hybrid RL |
| Machine + Monitoring Data | DL |
| | Hybrid RL |
| | DL + Hybrid RL |

Certain examples deploy learned models in a live system for patient monitoring. Training data is to match collected data, so if live data is being collected during surgery, for example, the model is to be trained on live surgical data also. Training parameters can be mapped to deployed parameters for live, dynamic delivery to a patient scenario (e.g., in the operating room, emergency room, etc.). Also, one-dimensional (1D) time series event data (e.g., ECG, EEG, O2, etc.) is processed differently by a model than a 2D or 3D image. 1D time series event data can be aggregated and processed, for example.

Thus, as shown below, one or more medical devices can be applied to extract time-series data with respect to a patient, and one or more monitoring devices can capture and process such data. Benefits to one-dimensional, time-series data modeling include identification of more data-driven events to avoid false alarms (e.g., avoiding false alarm fatigue, etc.), provide quality event detection, etc. Other benefits include improved patient outcomes. Cost-savings can also be realized, such as reducing cost to better predict events such as when to reduce gas, when to take a patient off an oxygen ventilator, when to transfer a patient from operating room (OR) to other care, etc.

Other identification methods are threshold based rather than personalized. Certain examples provide personalized modeling, based on a patient's own vitals, machine data from a healthcare procedure, etc. For example, for patient heart rate, a smaller person has a different rate than heavier built person. As such, alarms can differ based on the person rather than conforming to set global thresholds. A model, such as a DL model, etc., can determine or predict when to react to an alarm versus turn the alarm off, etc. Certain examples can drive behavior, configuration, etc., of another machine (e.g., based on physiological conditions, a machine can send a notification to another machine to lower anesthesia, reduce ventilator, etc.; detect ventilator dystrophy and react to it, etc.).

As shown in an example system 100 of FIG. 1, one or more medical devices 110 (e.g., ventilator, anesthesia machine, intravenous (IV) infusion drip, etc.) administer to a patient 120, while one or more monitoring devices 130 (e.g., electrocardiogram (ECG) sensor, blood pressure sensor, respiratory monitor, etc.) gather data regarding patient vitals, patient activity, medical device operation, etc. Such data can be used to train an AI model, can be processed by a trained AI model, etc.

Figure 2A:
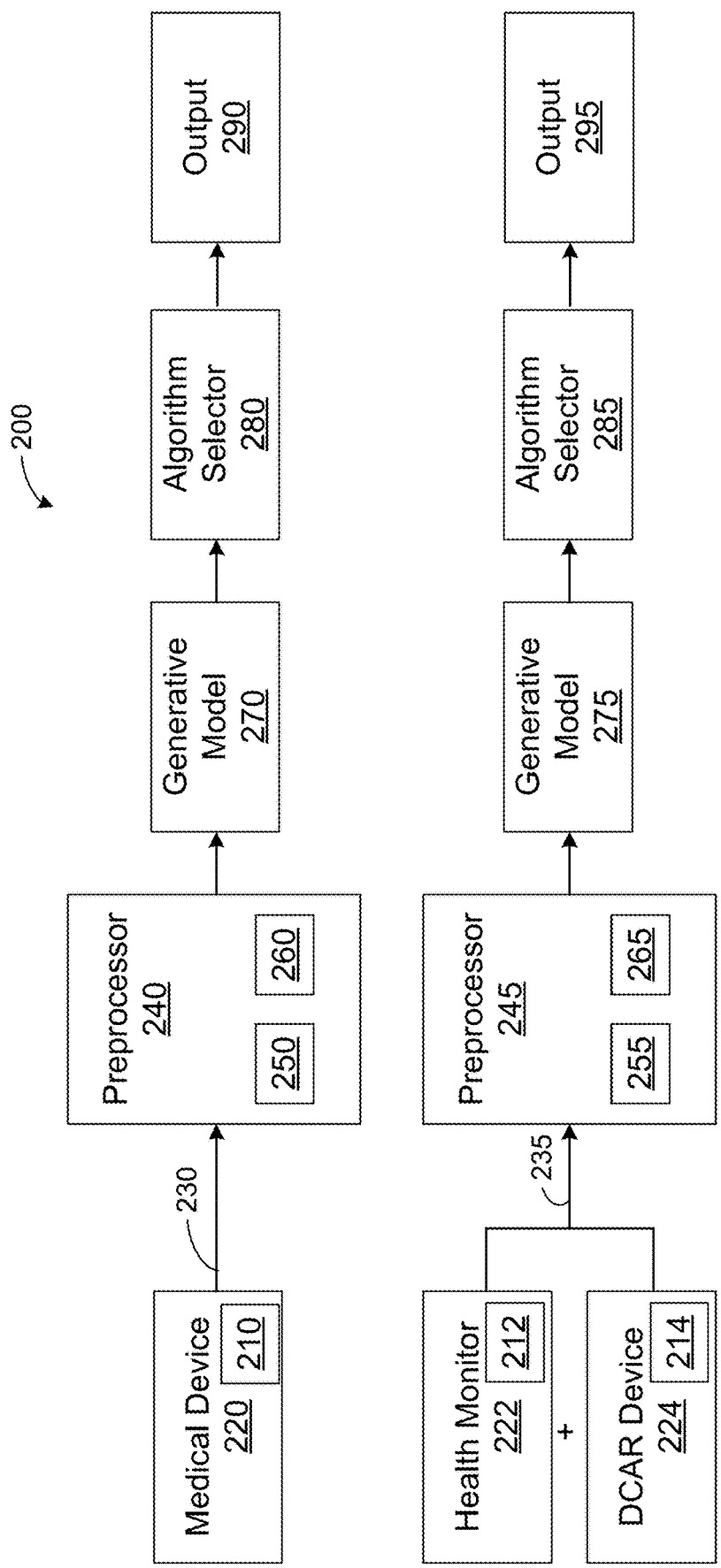
FIGS. 2A-2D are block diagrams of example systems to generate synthetic one-dimensional time-series data.

Certain examples provide systems and methods for missing data imputation of machine and/or physiological vitals data using AI model(s). For example, as shown in an example system 200 of FIG. 2A, machine data 210 and physiological (e.g., vitals, etc.) data 212, 214 can be captured from one or more medical devices 220, mobile digital health monitors 222, one or more diagnostic cardiology (DCAR) devices 224, etc., is provided in a data stream 230, 235 (e.g., continuous streaming, live streaming, periodic streaming, etc.) to a preprocessor 240, 245 to pre-process the data and apply one or more machine learning models 250, 255 (e.g., AI models, such as a DL model, a hybrid RL model, a DL+hybrid RL model, etc.) to detect events (e.g., heart attack, stroke, high blood pressure, accelerated heart rate, etc.) in a set of real data 260, 265 formed from the data stream 230, 235, etc., for example.

The pre-processed data is provided from the preprocessor 240, 245 to a generative model 270, 275. The generative model 270, 275 is an unsupervised learning model that processes the data from the preprocessors 240, 245 to determine or "learn" a data distribution of the training set from which the model 270, 275 can generate additional data points including variation from the training data set. The generative model 270, 275 models a distribution that is as similar as possible to the true data distribution of the input data set. Example generative models 270, 275 include a variational autoencoder (VAE), generative adversarial network (GAN), etc.

For example, a VAE tries to maximize a lower bound of a data log-likelihood, and the GAN tries to achieve an equilibrium between generator and discriminator. The VAE provides a probabilistic graph model to learn a probability distribution of the data input to the model 270, 275 (e.g., the training data set). Latent variables inferred from the data by the VAE model can be assumed to have generated the data set and can then be used to generate additional data such as to enlarge the data set, impute missing data from a time series, etc.

A GAN employs a game theory-style approach to find an equilibrium between a generator network and a discriminator network, for example. A generator network model learns to capture the data distribution, and a discriminator network model estimates a probability that a sample came from the data distribution rather than from a model distribution. As such, the generator network is to generate realistic data, and the discriminator network is to determine whether the generated data is real or fake. In some examples, such as the example of FIG. 2A, the generative model 270, 275 is already trained and operates in an inferencing mode to fill in missing data and/or events when possible.

An output of the generative models 270, 275 (e.g., the real data 260, 265 supplemented by synthetic data generated by the generative models 270, 275, etc.) is provided to an algorithm selector 280, 285, which selects, based on one or more parameters, settings, criteria, etc., whether to predict an event, detect an event, classify an event, etc. The selected algorithm (e.g., an AI model-based algorithm, such as using a DL model, a hybrid RL model, a DL+hybrid RL model, etc.) 280, 285 is used to process the combined data set to produce an output 290, 295. The output 290, 295, can include one or more insights, alerts, actions, etc., for a system, machine, user, etc. For example, the output 290, 295 can include a prediction, based on model(s) applied to the streaming 1D data, of an occurrence of event(s) such as heart attack, stroke, high blood pressure, accelerated heart rate, etc., and an actionable alert can be provided by the output 290, 295 to adjust an intravenous (IV) drip, activate a sensor and/or other monitor, change a medication dosage, obtain an image, send data to another machine to adjust its settings/configuration, etc.

Figure 2B:
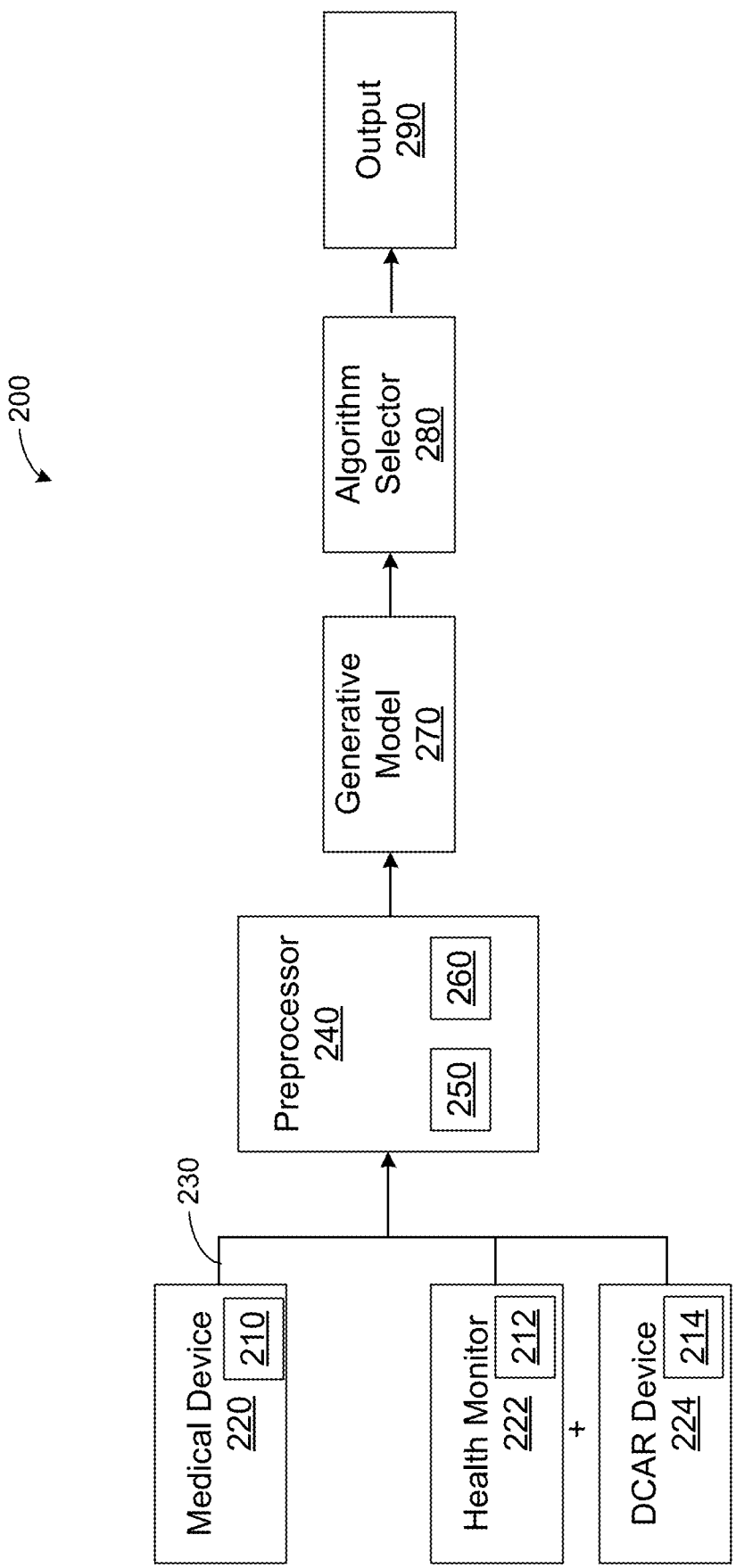

FIG. 2B illustrates an example implementation of the system 200 in which the data 210-214 from sources 220-224 is provided as a single stream 230 to the preprocessor 240 including machine learning model(s) 250 to form a real data set 260 to be provided to the generative model 270. An output of the generative model 270 (e.g., the real data 260 supplemented by synthetic data generated by the generative model 270 to infer missing data from a time series, etc.) is provided to the algorithm selector 280, which selects, based on one or more parameters, settings, criteria, etc., whether to predict an event, detect an event, classify an event, etc. The selected algorithm (e.g., an AI model-based algorithm, such as using a DL model, a hybrid RL model, a DL+hybrid RL model, etc.) 280 is used to process the combined data set to produce an output 290. The output 290 can include one or more insights, alerts, actions, etc., for a system, machine, user, etc.

Figure 2C:
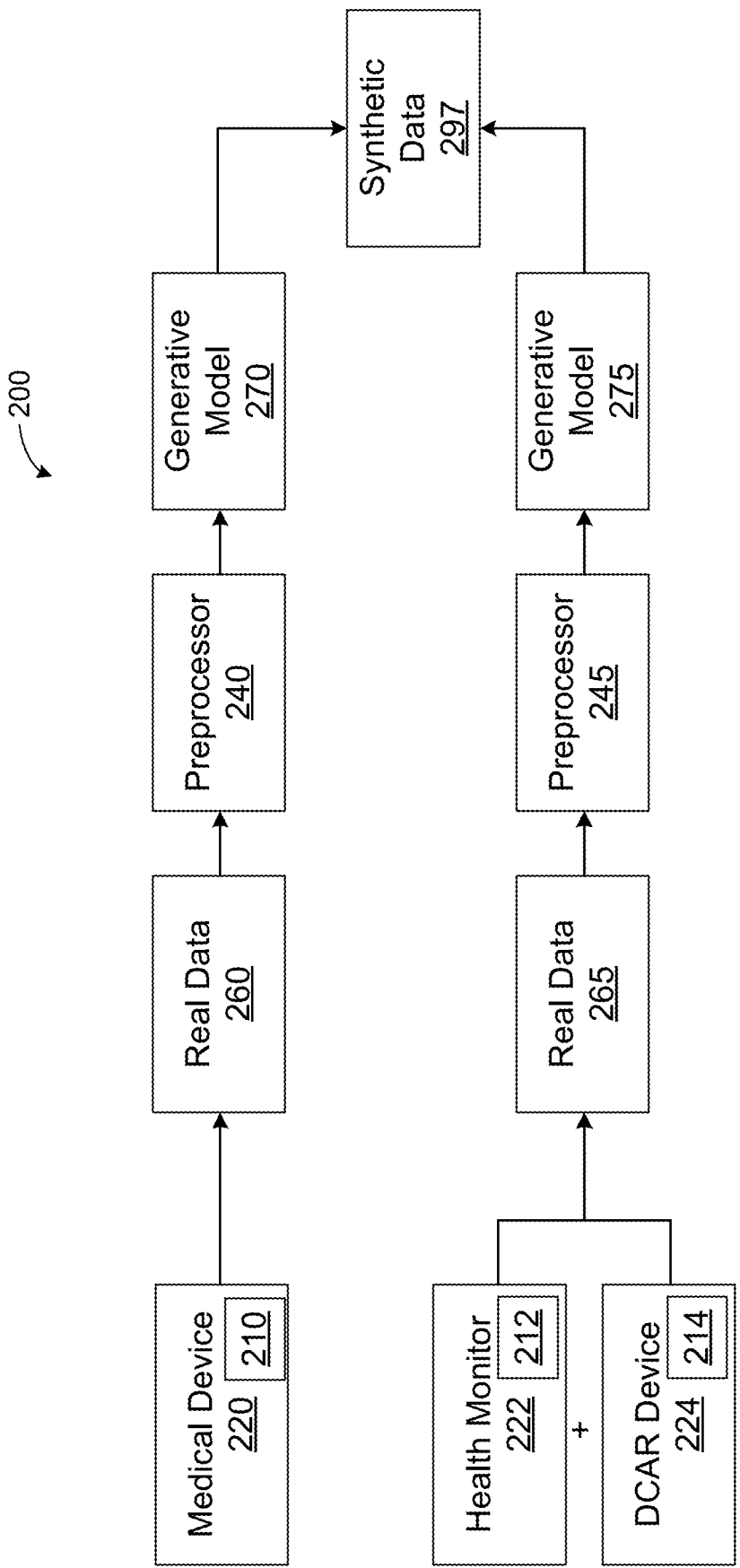

In certain examples, such as shown in FIG. 2C, data 210-214 from sources 220-224 can be collected offline to form sets of real data 260, 265. In some examples, only machine data 210 is collected. In other examples, only physiological data 212, 214 is collected. In other examples, both machine data 210 and physiological data 212, 214 are collected to form the real data 260, 265. The preprocessor 240, 245 pre-processes the data and adds annotations to events in the data 260, 265 by apply one or more machine learning models (e.g., AI models, such as a DL model, a hybrid RL model, a DL+hybrid RL model, etc.) to events detected in the set of real data 260, 265, for example.

An annotation adds a label, indication, explanation, detail, etc., associated with the time-series data to enable the data to be understood and used for training, testing, etc., of one or more AI models. The annotations impart an understanding to associated data and can serve to identify one or more events occurring in association with points in the stream or sequence of data, for example. For example, an annotation can indicate a red alarm occurring at a point in the time series of waveform data. Alarms, non-alarms, and/or other events can be indicated via annotation, for example. While, in some examples, expert analysts create annotations from a review of the data, certain examples generate synthetic annotations along with the synthetic data.

The pre-processed data is provided from the preprocessor 240, 245 to the generative model 270, 275. The generative model 270, 275 is an unsupervised learning model that processes the data from the preprocessors 240, 245 to determine or "learn" a data distribution of the training set from which the model 270, 275 can generate additional data points including variation from the training data set, for example. The generative model 270, 275 generates additional data and associated events to form synthetic data 297, which can be output for model training, model testing, etc., such as in connection with AI model training, testing, and deployment for 1D time series data related to a patient, medical equipment, etc.

In certain examples, a first phase of the system 200 of FIG. 2C operates in a training mode with the preprocessor 240, 245 and generative model 270, 275 to train the generative model 270, 275 with real data 260, 265. Then, in a second phase, the system 200 operates in an inferencing mode to leverage the generative model 270, 275 to generate synthetic time-series data and corresponding events 297.

Figure 2D:
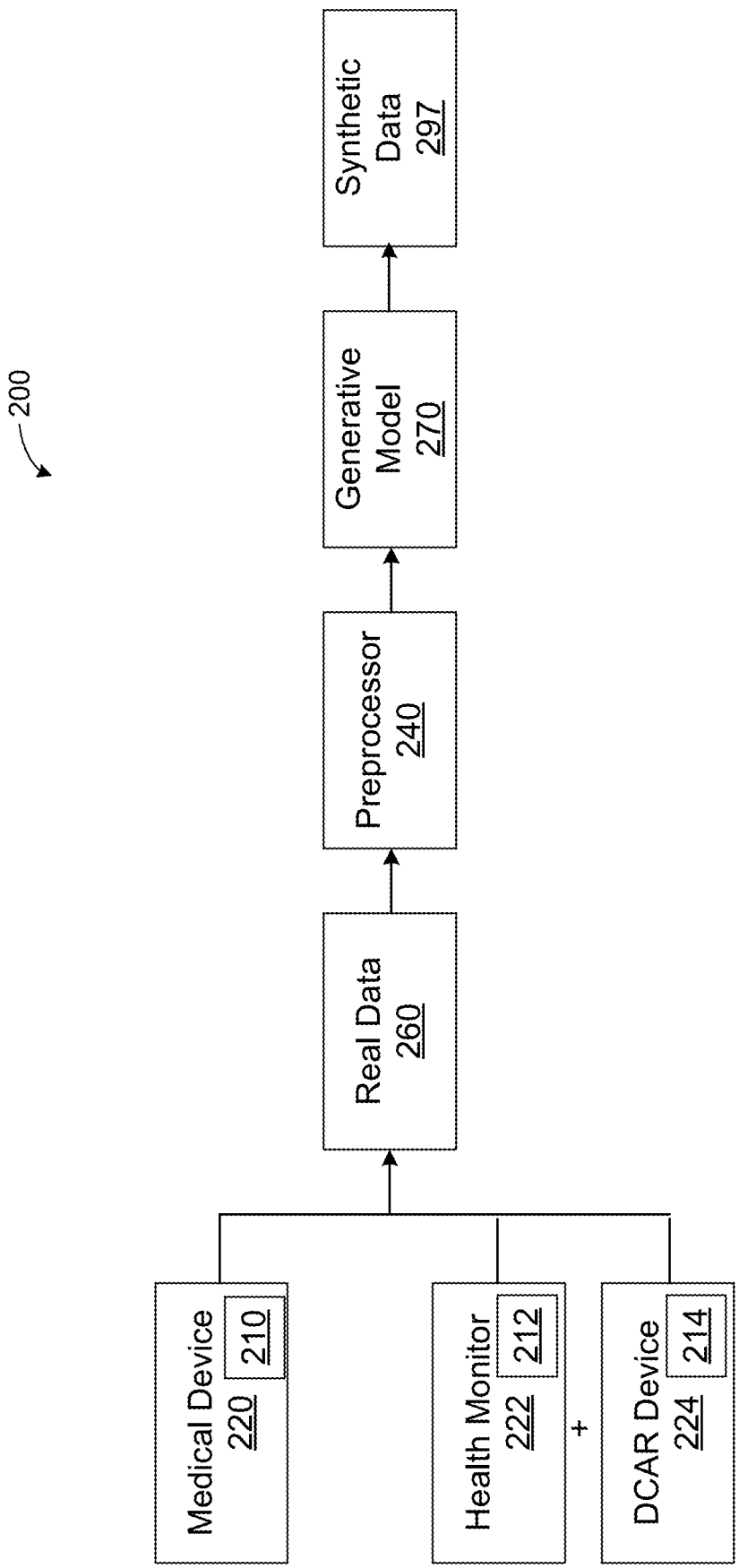

FIG. 2D illustrates an example implementation of the system 200 in which the data 210-214 from sources 220-224 is provided as a single data set collected offline to form the real data 260. The preprocessor 240 pre-processes the data and adds annotations to events in the data 260 by apply one or more machine learning models (e.g., AI models, such as a DL model, a hybrid RL model, a DL+hybrid RL model, etc.) to events detected in the set of real data 260, for example. The pre-processed data is provided from the preprocessor 240 to the generative model 270 to generate additional data points including variation from the training data set, for example. The generative model 270, 275 generates additional data and associated events to form synthetic data 297 (e.g., to supplement a data set, to impute missing data in a waveform and/or other time series, etc.), which can be output for model training, model testing, etc., such as in connection with AI model training, testing, and deployment for 1D time series data related to a patient, medical equipment, etc.

In certain examples, a first phase of the system 200 of FIG. 2D operates in a training mode with the preprocessor 240, 245 and generative model 270, 275 to train the generative model 270, 275 with real data 260, 265. Then, in a second phase, the system 200 operates in an inferencing mode to leverage the generative model 270, 275 to generate synthetic time-series data and corresponding events 297.

Figure 3:
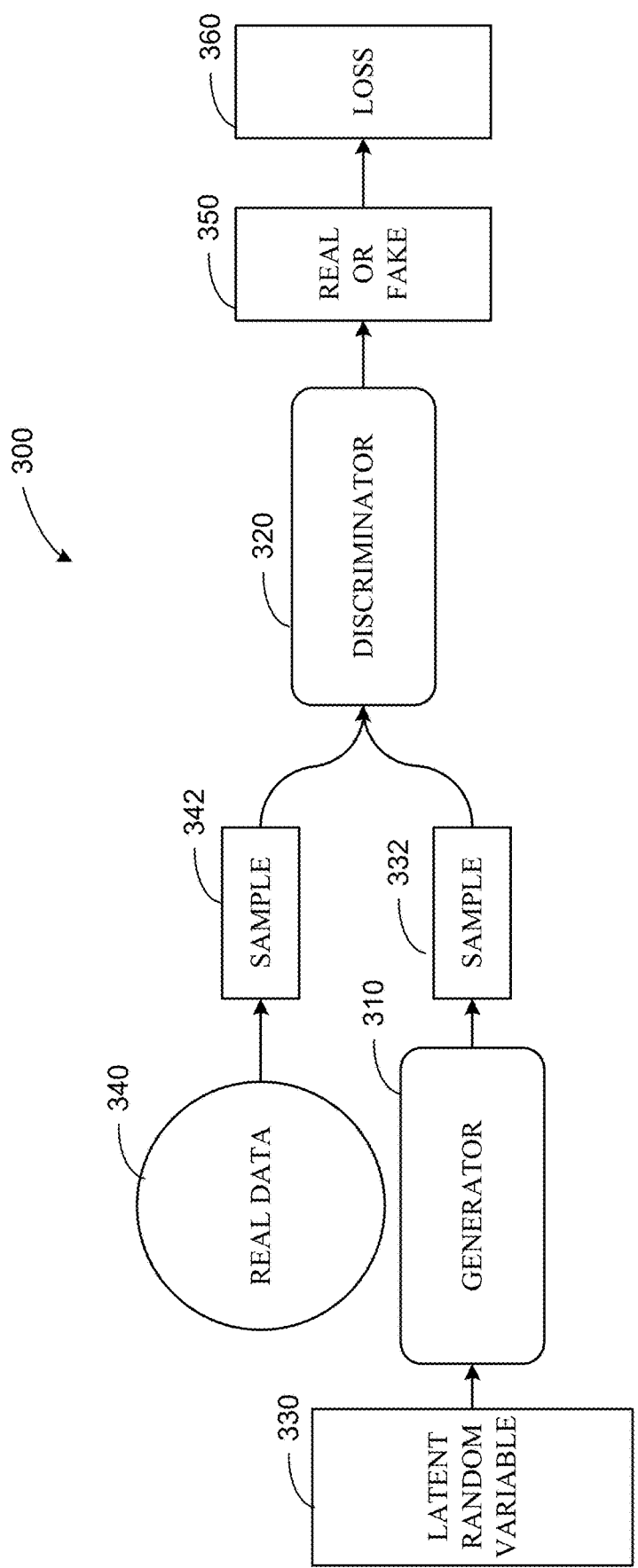
FIG. 3 shows elements of an example generative adversarial network architecture.

As discussed above, the generative network(s) 270, 275 can be implemented using a GAN. In certain examples, a GAN includes two networks: a generator network and a discriminator (also referred to as a critic) network. The generator network produces a sample, such as a waveform, other time series, etc., from a latent code (e.g., an output of an encoder of the GAN that maps a waveform or portion thereof to a corresponding code, etc.), and a distribution of such data can be indistinguishable from a training distribution. Since it is generally infeasible to engineer a function to determine whether the generator network distribution is indistinguishable from a training distribution, the discriminator network is trained to do the assessment of the generator network distribution. Since networks are differentiable, a gradient can be generated to steer both networks to the right direction. In certain examples, the generator is of main interest; the discriminator is an adaptive loss function that gets discarded once the generator has been trained. FIG. 3 shows elements of an example GAN architecture 300. In certain examples, high-quality synthetic time series data can be generated by the example GAN architecture 300 using one or more GAN algorithms such as a progressively growing GAN algorithm (e.g., by Nvidia, etc.), etc.

The example GAN architecture 300 shown in FIG. 3 includes a generator 310 and a discriminator 320. The example generator 310 (e.g., generator neural network) receives a latent random variable 330 and produces a first sample 332 (e.g., a first time series or portion thereof, etc.) by processing the latent random variable 330. Real or actual data 340 can provide a second sample 342 (e.g., a second time series or portion thereof, etc.), and the real data sample 342 and generator sample 332 are processed by the discriminator 320 to determine whether or not the sample time series data 332 is real or fake 350 compared to the actual time series data sample 342. Based on the outcome 350 determined by the discriminator 320, a loss 360 can be determined. For example, if the discriminator 320 sees a difference (e.g., fake or synthetic) between the real time series data sample 342 and the synthetic time series data sample 332, then a loss 360 in synthetic data quality through the generator 310 can be determined. Such loss or error 360 (e.g., in the form of a gradient or other adaptive loss function, etc.) can be used to generate additional synthetic data, adjust operation of the generator 310, etc.

As such, certain examples generate robust and validated synthetic data to avoid invalid correlations and/or other failures stemming from inadequate data resulting in improper, inaccurate networks which can lead to failures threatening patient health and safety, etc. For example, lack of sufficient data for training and testing can render a neural network model incomplete and/or inaccurate, resulting in erroneous output, improper correlation, etc. Alternatively or in addition, data missing from a time series waveform can cause a neural network model to malfunction when data missing from the waveform is expected to be processed as part of an input set. Using the synthetic data, scalable AI models can be generated and deployed for applications such as patient event detection, event prediction, event classification, clinical care, radiopharmaceutical generation, etc. The AI models can implement algorithms to be deployed on medical devices to achieve precision healthcare for patients, for example.

For a deep learning task, data can be divided into a plurality of groups, and GANs can be trained on the data. A global network can then be trained on the data generated by the GANs. Compared to a network trained only on native data, the global, GAN-driven network trained on synthetic data or a combination of real and synthetic data (e.g., a 1:1 combination, etc.) can provide better performance compared to a network trained only using real data.

In certain examples, a GAN generates synthetic data based on one or more random number floating point vectors between 0 and 1, even with training based on real data. Using the synthetic data generator, an infinite number of time series data can be generated. Such one-dimensional data has realistic values but does not necessarily duplicate any of the actual time series used in the training. Thus, actual patient data can be used to generate realistic synthetic data that does not correspond to the actual patient data. Patient privacy and security can be protected while providing realistic, synthetic data to train and/or test the AI models.

Figure 4:
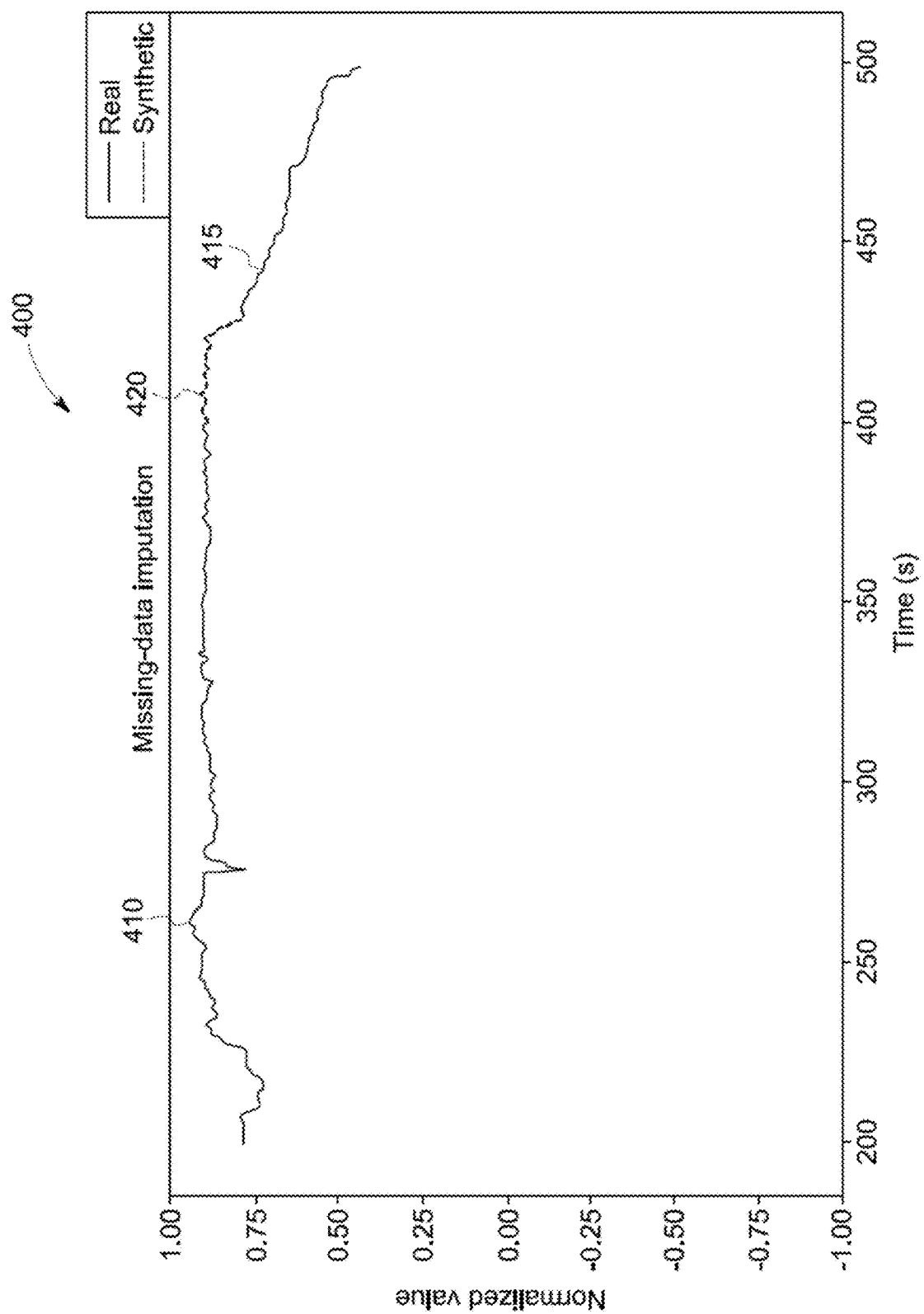
FIG. 4 illustrates an example of missing data imputation in a waveform.

FIG. 4 shows an example of a missing data imputation for a time-series waveform 400 using a generative model. As shown in the example of FIG. 4, real data 410, 415 forming the waveform 400 has a portion of missing data that is filled by imputation with synthetic data 420 generated by one or more generative models 270, 275, for example. As such, another AI model expecting to process a complete waveform 400 now has a complete waveform 400 to process with the addition of the synthetic data 420 filling in the gap of the real data 410, 415. The missing data can result from signal loss, data corruption, interruption in monitoring, etc., and synthetic data can be imputed to complete the waveform, for example.

Figure 5:
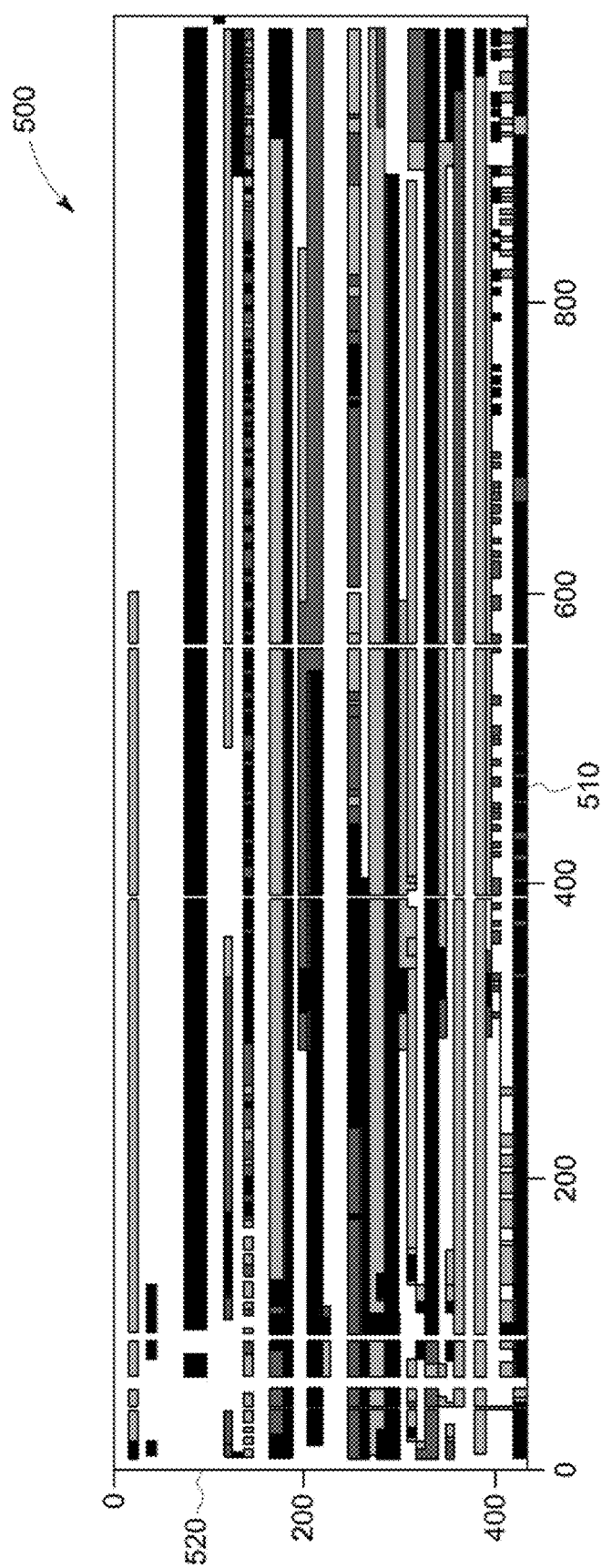
FIG. 5 shows an example of multi-channel time-series data.

Alternatively or in addition to data imputation, certain examples use generative models to generate corresponding events (e.g., annotations) along with synthetic, multi-channel, time-series data for clinical use cases. For example, in addition to or instead of single channel data, a time-series GAN can be used to generate multi-channel time-series physiological and/or machine data generation. Real data captured for a given patient is multi-channel, sourced from multiple sensors, etc., that are highly correlated. That is, each channel in a multi-channel data stream corresponds to a signal providing a univariate time series of one-dimensional signal data. The channels combine into a multi-channel data set providing multivariate time series data. Certain examples train, test, and deploy a GAN model to generate multi-channel synthetic data that can be used further for artificial intelligence (AI) model training. FIG. 5 shows an example of multi-channel time-series data 500, in which an x-axis 510 indicates a time, a y-axis 520 indicates variables (e.g., channels), and a color or pattern of each line, block, or segment represents a value of that variable at that point in time.

Certain examples provide simultaneous generation of corresponding events and/or other annotations with generation of multi-dimensional time-series physiological/machine data. The generated synthetic events function as annotations that can be used further for training event prediction, classification, and/or detection models. In some examples, k events can be encoded as time series data over k channels to learn, using one or more GANs and/or other generative models, a distribution of (n+k) variables/channels, where n is a number of channels for real time-series data. In such examples, real, measured data can be obtained from one or more sensors, monitors, etc., for n variables (e.g., real, multi-channel, time-series data, etc.) and a corresponding k events (e.g., annotations, etc.), such as shown in the example of FIG. 5. Synthetic annotations can be generated for events external to a 1D time series data signal, such as introduction of anesthetic gases, turning gas on/off, etc. Synthetic annotations can also be generated for events internal to a 1D time series data signal, such as events from physiological signals such as an R-wave from an ECG, etc. Example events can include one or more case, maintenance, flow, agent, emergency, etc., events such as shown in the example of Table 1.

Figure 6A:
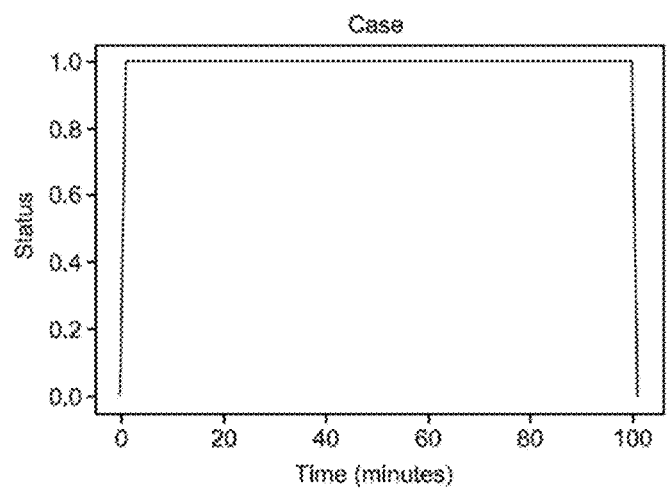
FIGS. 6A-6C show example events converted to time signals.
Figure 6B:
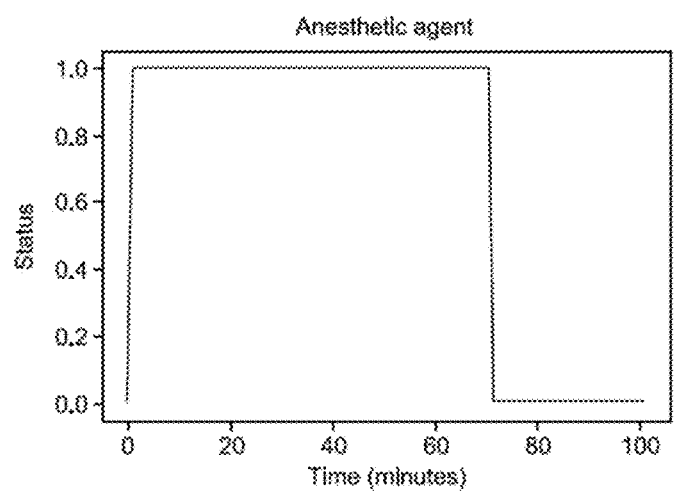
Figure 6C:
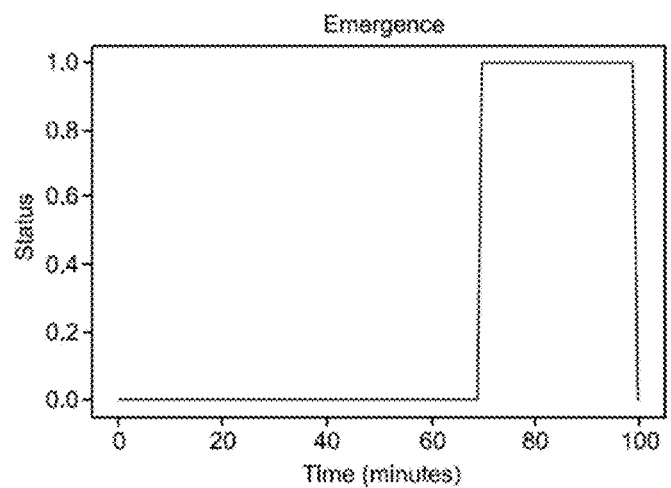
Figure 7:
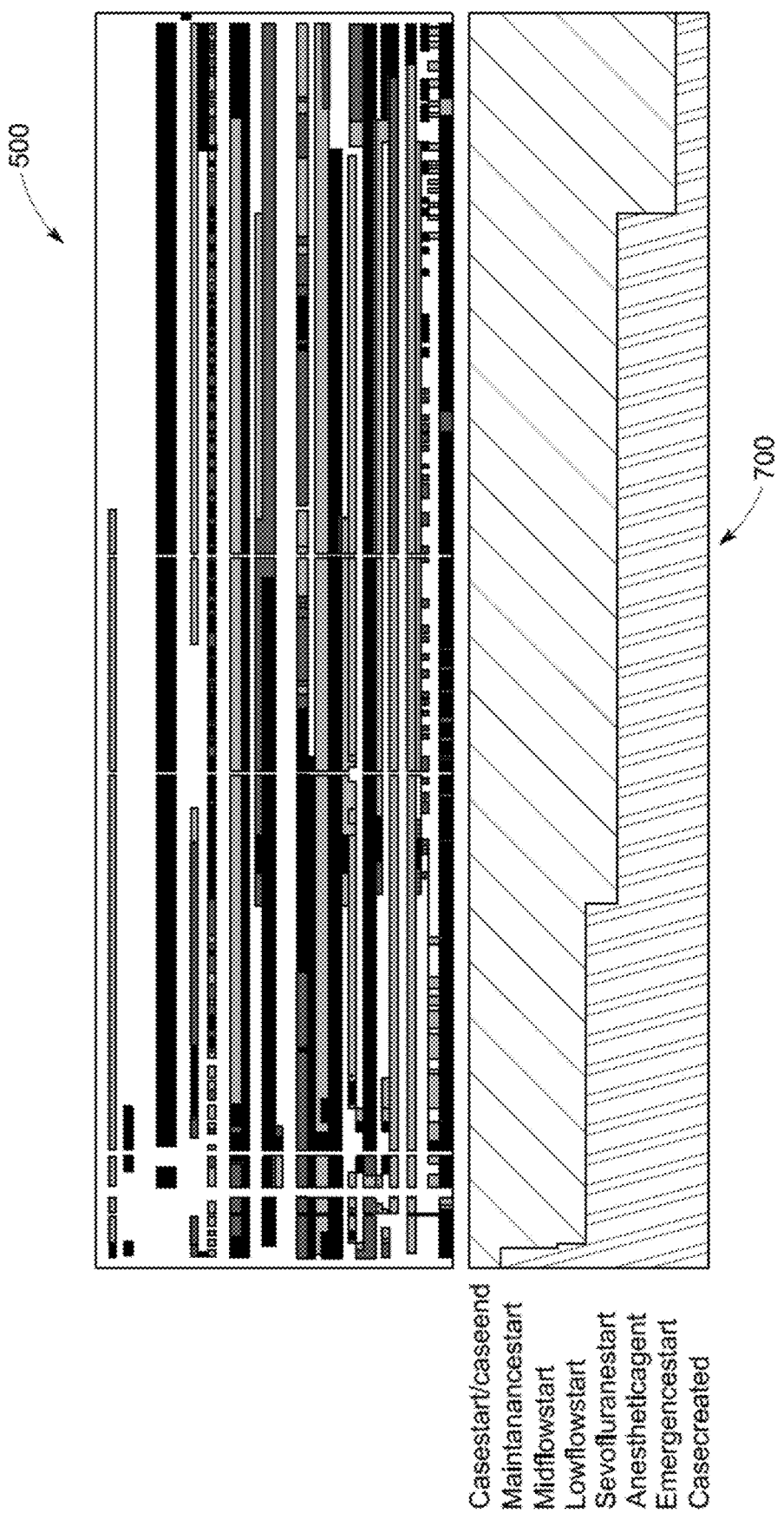
FIG. 7 shows both multi-channel data and events represented as time-series signals.

'Case', 'HighFlow', 'LowFlow', 'Maintenance', 'Sevoflurane', 'Emergence', 'AnestheticAgent', etc., are events in this case. A Start and End of any event can be presented as rise (low-to-high) and fall (high-to-low) transition of the associated signal, respectively. For example, FIGS. 6A-6C show example events converted to time signals. The example of FIG. 6A depicts a case over a time period. The example of FIG. 6B depicts an anesthetic agent event during the time period. The example of FIG. 6C depicts an emergency event during the time period. FIG. 7 shows both the multi-channel data 500 (see, e.g., FIG. 5) and events 700 represented as time-series signals.

Once the generator model is trained, the generator model can generate (n+k) channels of data. A last k channels of the n+k channels can be decoded and converted back to human-readable events. The data and events can be further verified using one or more training-testing methods.

In some examples, conditional GANs operate on an input provided to specify a condition and/or class to be generated by the GAN. For example, a user can define and instruct the trained GAN to generate images of a number '5'. However, in certain examples, a time-series GAN (t-GAN) is to learn and generate multi-channel time-series data along with multiple corresponding events from the same distribution. As such, both time-series data and corresponding events distribution can be learned while training the t-GAN.

Further, the conditional GAN does not address a multi-label, multi-class problem. Conversely, in certain examples, the trained generator produces multiple events along with the data, wherein a start, stop, and duration of these events may vary widely. Certain examples generate multiple channels of physiological and/or machine data and associated events for training and testing of neural networks and/or other AI models.

As such, certain examples generate 1D time-series data using one or more recurrent GANs. During training, the generator network learns a distribution of medical time-

TABLE 1

Captured Event Examples

| source_id | event_datetime | event_code | datetime |
|---|---|---|---|
| Device 2 | 2018 Jan. 15 07:30:01.832000 | CaseStart | 2018 Jan. 15 07:30:01.832 |
| Device 2 | 2018 Jan. 15 07:30:44.683000 | MaintenanceStart | 2018 Jan. 15 07:30:44.683 |
| Device 2 | 2018 Jan. 15 07:30:44.683000 | MidFlowStart | 2018 Jan. 15 07:30:44.683 |
| Device 2 | 2018 Jan. 15 07:30:56.715000 | LowFlowStart | 2018 Jan. 15 07:30:56.715 |
| Device 2 | 2018 Jan. 15 07:31:40.884000 | LowFlowStart | 2018 Jan. 15 07:31:40.884 |
| Device 2 | 2018 Jan. 15 07:34:57.898000 | MidFlowStart | 2018 Jan. 15 07:34:57.898 |
| Device 2 | 2018 Jan. 15 07:34:57.898000 | MaintenanceStart | 2018 Jan. 15 07:34:57.898 |
| Device 2 | 2018 Jan. 15 07:35:17.925000 | LowFlowStart | 2018 Jan. 15 07:35:17.925 |
| Device 2 | 2018 Jan. 15 07:36:30.312000 | MaintenanceStart | 2018 Jan. 15 07:36:30.312 |
| Device 2 | 2018 Jan. 15 07:36:30.312000 | MidFlowStart | 2018 Jan. 15 07:36:30.312 |
| Device 2 | 2018 Jan. 15 07:37:10.473000 | LowFlowStart | 2018 Jan. 15 07:37:10.473 |
| Device 2 | 2018 Jan. 15 07:38:34.558000 | LowFlowStart | 2018 Jan. 15 07:38:34.558 |
| Device 2 | 2018 Jan. 15 07:47:52.330000 | LowFlowStart | 2018 Jan. 15 07:47:52.330 |
| Device 2 | 2018 Jan. 15 07:47:52.330000 | SevofluraneStart | 2018 Jan. 15 07:47:52.330 |
| Device 2 | 2018 Jan. 15 08:23:59.001000 | AnestheticAgentEnd | 2018 Jan. 15 08:23:59.001 |
| Device 2 | 2018 Jan. 15 08:23:59.001000 | EmergenceStart | 2018 Jan. 15 08:23:59.001 |
| Device 2 | 2018 Jan. 15 08:34:10.396000 | CaseEnd | 2018 Jan. 15 08:34:10.396 |
| Device 2 | 2018 Jan. 15 08:34:10.396000 | CaseCreated | 2018 Jan. 15 08:34:10.396 |

Training data can be processed to form modified real training data. The modified training data is used to train a multi-channel GAN model, for example. The GAN model learns a distribution of the multi-variate data along with its corresponding events. For example, as shown in Table 1, series data. The trained model can be used to generate and also to reconstruct multi-variate medical time series data for the usage of Artificial Intelligence (AI) model development. For supervised AI model development, the data must be annotated by a domain expert before the training takes place.

To address this problem in synthetic data generation, certain examples generate corresponding multi-channels such as annotation channels using annotated multivariate time-series data in the training. Once the generator is trained, generated synthetic data can be used to train a clinical model to address problems such as data imbalance, missing data, limited data accessibility, etc.

Figure 8:
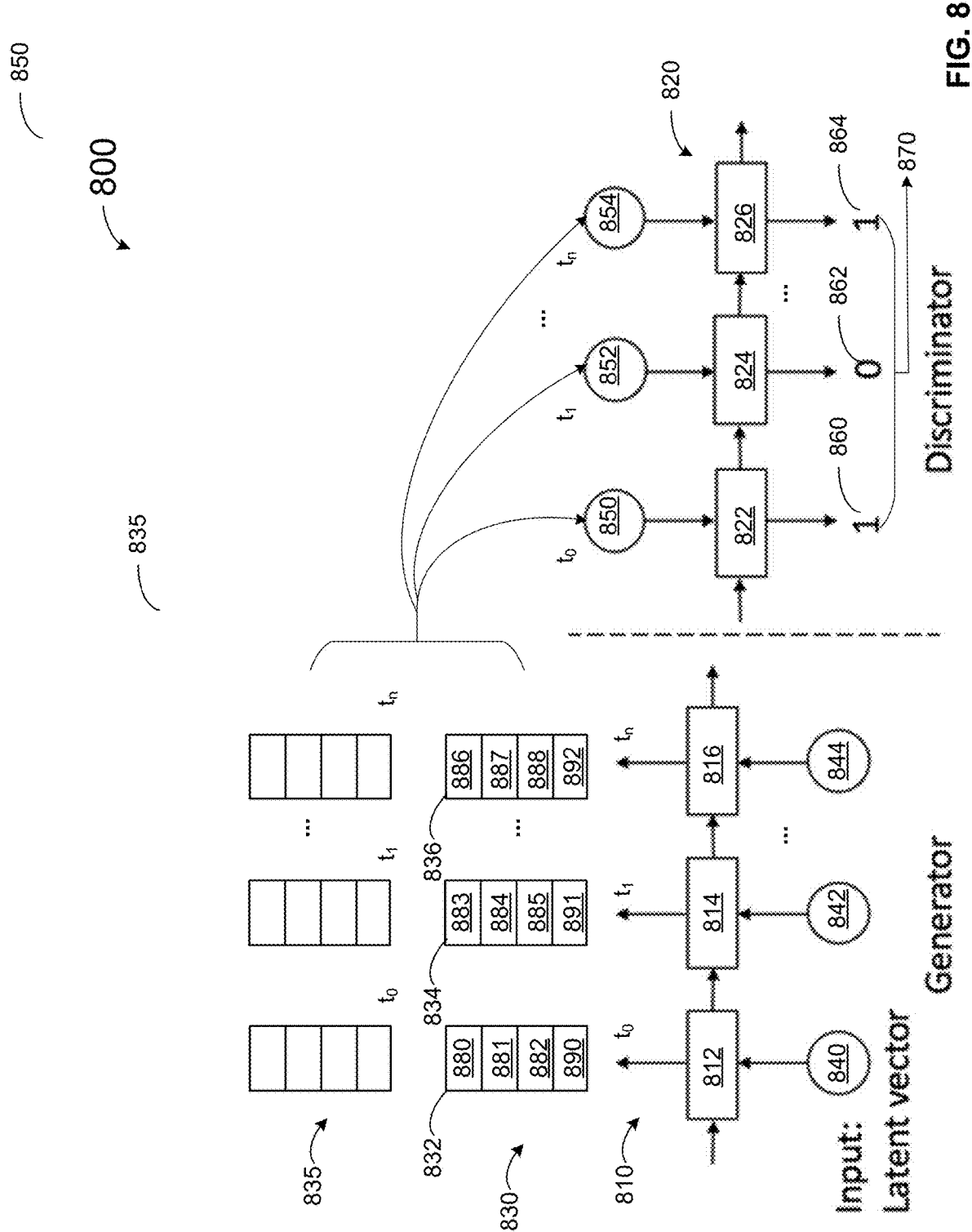
FIG. 8 depicts an example generative adversarial network model.

An example architecture of a recurrent GAN model 800 is shown in FIG. 8. In the example of FIG. 8, a generator 810 is to produce a time-series sequence of a pre-defined sequence length. A discriminator 820 is to determine whether a sequence is from a model-based distribution (e.g., "fake" or synthetic) or from a "real" data distribution. Both generator 810 and discriminator 820 models utilize long-short term memory (LSTM) circuits, for example. The LSTM circuits can be based on a convolutional neural network, recurrent neural network, other machine learning network, etc. The generator 810 can be used to generate an individual, synthetic, single-channel signal or a synthetic N-channel signal depending upon its configuration, input parameter(s), trigger, etc. The generator 810 can generate synthetic annotations for events external to a 1D time series data signal, such as introduction of anesthetic gases, turning gas on/off, etc., and/or for events internal to a 1D time series data signal, such as events from physiological signals such as an R-wave from an ECG, etc.

As shown in the example of FIG. 8, the generator 810 can generate a multi-channel synthetic data signal 830 by passing random noise in a latent input vector 840-844 through a plurality of LSTM circuits 812-816 to generate synthetic data signal samples 832-836, while the discriminator 820 is trained to identify a real or synthetic sequence from an input 850-854 and output 860-864, using LSTM circuits 822-826, one or zero respectively for each time step. The final decision of overall sequence 870 is obtained by voting on each time-step for real/synthetic identification as shown in the example of FIG. 8. The voting and/or other decision-making can be determined using a decision aggregator implemented using one or more of majority pooling, mean, median, other probability-based approach, etc. Thus, the discriminator 820 classifies the generated synthetic data set 830 with a first classification (e.g., "fake" or synthetic) or a second classification (e.g., "real") that can be used as feedback to tweak/train the generator 810 to produce realistic synthetic data 830 usable for training, testing, and/or other generation of AI models, data imputation, etc.

As shown in the example of FIG. 8, latent vector(s) 840-844 are input to the LSTM circuits 812-816 to generate the multi-channel synthetic data series 830. The latent vectors 840-844 represent random noise and/or other data distribution of values (e.g., a probability distribution of signal data variation, etc.) to be used by the circuits 812-816 to form synthetic data values 830. Each circuit 812-816 contributes to the synthetic time series data 830 with a multi-channel portion 832-836 for a particular point in time $t_0, t_1, \ldots t_n$. The set of time series data portions, segments, or snapshots 832-836 at times $t_0, t_1, \ldots t_n$ form the multi-channel synthetic data stream 830. Each portion 832-836 includes a plurality of channels 880-892. The channels 880-892 include data channels 880-888 and annotation or event channels 890-892. Each data channel 880-888 represents a different source of the time series data (e.g., a different sensor, monitor, etc., providing a waveform such as an ECG, SpO2, brain activity, etc.). The annotation channels 890-892 indicate an event and/or other trigger occurring at a same point in time $t_0, t_1, \ldots t_n$ as the data in the corresponding data channels 880-888, for example. As such, the circuits 812-816 generate multiple channels 880-888 of synthetic 1D time series data along with an additional channel 890-892, at each point in time $t_0, t_1, \ldots t_n$, providing a synthetically-generated event 890-892 associated with the time series data 880-888. Together, the time series data 880-888 and associated event annotations 890-892 over times $t_0, t_1, \ldots t_n$ form the synthetic data stream 830. This synthetic data stream 830 can be compared to a real, captured multi-channel time series data stream 835 by the discriminator 820.

The synthetic data stream 830 and a stream of actual, collected time series data 835 are provided as paired inputs 850-854 for each time $t_0, t_1, \ldots, t_n$ to be processed by the circuits 822-826 to determine whether the input 850-854 is real or fake. As such, the LSTM circuits 822-826 determine, based on the real data 835, whether the time samples of synthetic data 832-836 match characteristics, format, appearance, pattern, etc., of the real data 835. The circuits 822-826 provide an output 860-864 indicative of a "vote" or classification 870 by the discriminator 820 as to whether the data stream 830 is "real" or "fake"/synthetic. This output 870 can determine whether or not the synthetic data stream 830 is suitable for use in training, testing, and/or otherwise developing AI models, for example.

Thus, initially, the synthetic data series 830 may resemble random noise (e.g., based on the latent input vector 840-844, etc.), but, over time and based on feedback, the synthetic data series 830 comes to resemble the content and pattern of real data 835 such that the synthetic data 830 can be used in addition to and/or in place of real data 835 to train, test, and/or otherwise development AI models for deployment to process patient 1D time series waveform data, for example. Using the discrete output 860-864, corresponding to multi-channel data 832-836 at a particular time $t_0, t_1, \ldots, t_n$, generated by a particular circuit 812-816, the generator 810 can be tuned to produce more realistic synthetic data 830.

In certain examples, the circuit 822-826 can compute a loss function between the corresponding real 830 and synthetic 835 channel values 880-892. The loss or difference between the data determines the output 860-864 of the models. The loss represented in the output 870 can provide feedback to modify one or more parameters, settings, configuration, etc., of one or more circuits 812-816 and/or associated latent vectors 840-844. For example, the output 870 can include an error gradient to train components of the generator 810. In certain examples, the latent vectors 840-844 can be associated with a probability distribution of data modified by feedback 870 from the discriminator 820.

In certain examples, the apparatus 800 can operate in a training mode or an inference mode. In the training mode, the generator 810 is trained using the output 870 (and associated loss function, etc.) from the discriminator 820 to produce realistic synthetic data 830 usable for AI model training, for example. In the inference mode, the discriminator 820 can be deactivated and/or otherwise ignored/discarded to allow the generator 810 to generate and output synthetic data 830 including waveform data values and annotation indicators for use by one or more AI models and/or associated generators/trainers unless/until feedback and/or an external input triggers retraining/modification of the generator 810, for example.

Thus, the example apparatus 800 employs concurrent time series 880-888 and corresponding auxiliary 890-892 data to improve annotation of time series patient waveform data. Synthetic annotation accompanying time series 1D data allows AI models to be trained to identify events associated with the time series data.

Figure 9:
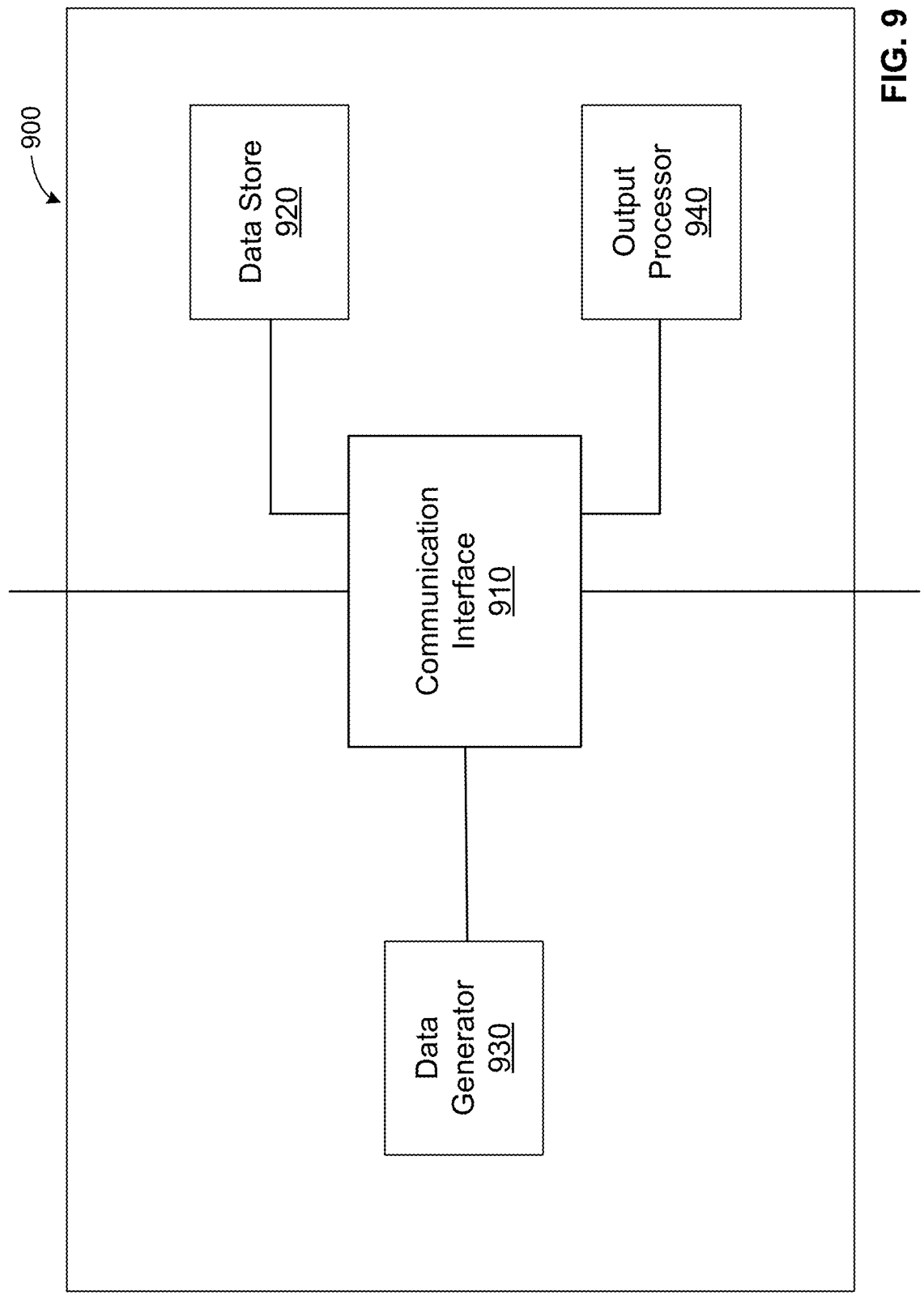
FIG. 9 illustrates an example synthetic data generator apparatus.

FIG. 9 illustrates an example synthetic data generator apparatus 900 including a communication interface 910, a data store 920, a 1D data generator 930, and an output processor 940. In the example of FIG. 9, the apparatus 900 receives input data (e.g., machine data 210 and physiological (e.g., vitals, etc.) data 212, 214 can be captured from one or more medical devices 220, mobile digital health monitors 222, one or more diagnostic cardiology (DCAR) devices 224, etc.) via the communication interface 910 (e.g., a wireless interface (e.g., WiFi™, Bluetooth™, BLE™, near field communication, etc.) a wired interface (e.g., cable, other wire, etc.), and/or other interface to receive and send data, etc.). Data can be stored in the data store 920 (e.g., as a buffer, semi-permanently, temporarily until deleted/overwritten/erased/etc., using random access memory (RAM), flash memory, hard disk drive, etc.) for use by the 1D time series data generator 930, etc.

In the example apparatus 900, the 1D data generator 930 includes one or more AI models, such as a t-GAN, other GAN, etc., (e.g., the generative model 270, 275, GAN 300, 800 etc.), to process one-dimensional time series data to generate synthetic (e.g., artificial) data to impute missing data from a waveform (e.g., as shown in the example of FIG. 4, etc.), generate additional synthetic data for a training and/or testing data set (e.g., as shown in the example data set 500 of FIGS. 5-6, etc.), etc. For example, the data generator 930 can be implemented using the example GAN apparatus 800 of FIG. 8. The synthetic data can be multi-channel data and can include a channel in which synthetic events, labels, and/or other annotations associated with the series data is also generated (e.g., as shown in the example of Table 1 and FIGS. 6A-7, etc.). In certain examples, correlation(s) between time series data channels are learned/identified and used to produce an event in an annotation channel. The correlated time series data/annotation output is provided by the output processor 940 to the communication interface 910 to be transmitted for storage and/or use, for example, in training an AI model, testing an AI model, imputing and/or interpolating missing data in an incomplete waveform, etc.

Figure 10:
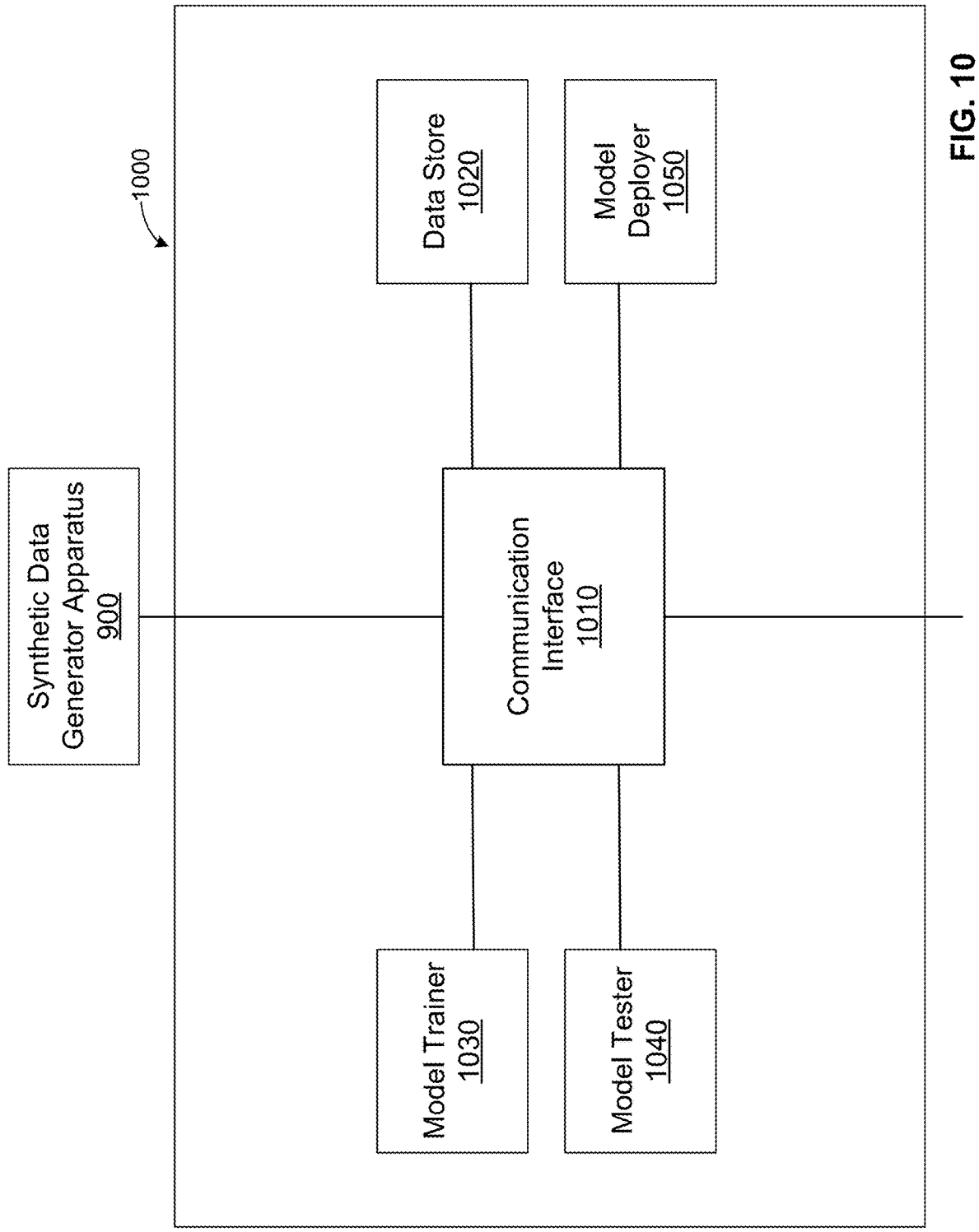
FIG. 10 illustrates an example model generator to leverage synthetic data from the apparatus of FIG. 9.

As shown in the example of FIG. 10, output from the output processor 940 can be provided to a model generator 1000 to train and test an AI model such as an RL network model, hybrid RL network model, other DL network model, etc. The example model generator 1000 includes a communication interface 1010 (e.g., a wireless interface (e.g., WiFi™, Bluetooth™, BLE™, near field communication, etc.) a wired interface (e.g., cable, other wire, etc.), and/or other interface to receive and send data, etc.), a data store 1020 (e.g., a RAM, flash memory, hard disk drive, etc.), a model trainer 1030, a model tester 1040, and a model deployer 1050. Synthetic data provided by the apparatus 900 is received by the communication interface 1010 and stored (e.g., buffered, saved, etc.) in the data store 1020. The data can be used alone or in combination with other synthetic data, actual measured/monitored/captured data, etc., by the model trainer 1030 to train an AI model. Once trained, the model tester 1040 can use the synthetic data, alone or in combination with other synthetic data, real data, etc., to test that the trained AI model processes an input appropriately to achieve a desired or expected output. The tested, trained AI model can then be stored in the data store 1020, deployed by the model deployer 1050 for use by another device, system, apparatus, etc., for example.

Thus, the example apparatus 900 of FIG. 9 works with the model generator 1000 of FIG. 10 to enable modeling of data and processing of data channels to produce a synthetic time series data stream with associated annotation output. The synthetic output annotation is correlated among the various data channels and provided as synthetic data to be used with and/or substituted for actual data in training, testing, and/or otherwise formulating AI models, etc. As such, an expanded data set can be formed using synthetic data including synthetic annotations of the synthetic data automatically generated rather than requiring manual annotation. Alternatively or in addition, one or more 1D waveforms can be completed through synthetic imputation.

For example, synthetic time series data can be generated in the form of a sine wave. Noise can be added to the sine wave, and the amplitude can be adjusted. The change in amplitude can be indicative of an event occurring at that point in the sine wave. Other changes such as a change in phase, frequency, etc., can also be indicative of occurrence of an event at that point in time. A GAN can generate such an event along with the underlying data using one or more data channels and an associated annotation channel, for example.

For example, a GAN can be used to mimic a sensor measuring a waveform value (e.g., electrocardiogram (EEG), breathing/oxygen flow, pulse, etc.). the sensor can focus on an event, such as application of anesthesia, heart attack, stroke, other emergent condition, etc. If the waveform sign is high, then the event occurred. If the waveform signal is low, then the event did not occur. Such signals can be synthetically generated, for example (see, e.g., FIGS. 6A-6C). In some examples, a univariate signal provides a signal event per channel. In some examples, a multi-variate signal provides multiple events per channel and/or multiple channels. Such implementation can be changed based on type of data represented, for example.

For example, to evaluate performance of a recurrent GAN model for reconstruction, univariate datasets including waveforms such as sine wave, sawtooth, triangle, and rectangular waves can be evaluated. Nonlinear variations can be introduced by varying the amplitudes, frequencies, and phases. To evaluate the performance of an overall training of the recurrent GAN model, a reconstruction of a signal can be used. Signal reconstruction can also be used to detect an outlier in a signal. Extending to signal reconstruction of multivariate datasets shows that recurrent GAN models can efficiently learn to generate smooth and periodic multivariate signals.

For an interpolation analysis, latent vectors can be obtained from two or more samples in a sample space, and a plurality of latent vectors can be generated by interpolation in a latent space. The latent vectors are projected back into the sample space. For example, models can be trained to interpolate synthetic samples for oxygen saturation (SpO2), Sine+Square, electrocardiogram (EKG)+SpO2 datasets, etc.

For supervised learning tasks, there is a need of good quality annotated data. For medical time-series data, these annotations come in various forms such as events. The data generator 930 (more generally, the example apparatus 900, etc.) can be used to generate such annotations along with corresponding data. Annotations can be generated for time-series data including various waveforms such as sine, sawtooth, etc., and corresponding events including change in amplitude, phase, frequency, etc. Events can be preprocessed and encoded in additional annotation channels as square wave signals in which one indicates the presence of an event and zero indicates the absence of an event, for example. The GAN model learns a correlation among multiple time-series channels including annotation channels. To evaluate the model, a training data set can be reconstructed, and the model learns a correlation among several data points generates an event where an amplitude change occurs in the time-series data, for example.

Thus, an AI model, such as a recurrent GAN, etc., can effectively learn a pattern from an input signal with a periodic structure. In certain examples, annotations can be encoded with the signal data. In certain examples, missing data can be imputed. In certain examples, the AI model can be penalized in training using loss functions, etc.

Thus, certain examples supplement and/or replace 1D time series (e.g., waveform) data captured from one or more medical devices (e.g., ECG, EEG, ventilator, etc.) and a patient via one or more monitoring devices. Physiological data and other 1D time series signals can be indicative of a physiological condition associated with a body part from which the data is obtained (e.g., because the signal corresponds to electrical activity of the body part, etc.). As such, the time series physiological signal data, machine data, etc., can be processed for clinical decision making regarding a patient, medical equipment, etc. A variety of waveforms (e.g., ECG, heart rate (HR), respiratory gas movement, central venous pressure, arterial pressure, oxygen fraction, waveform capnography, etc.) can be captured and/or synthesized with respect to a patient, a group of patients, a patient population, etc.

Figure 11:
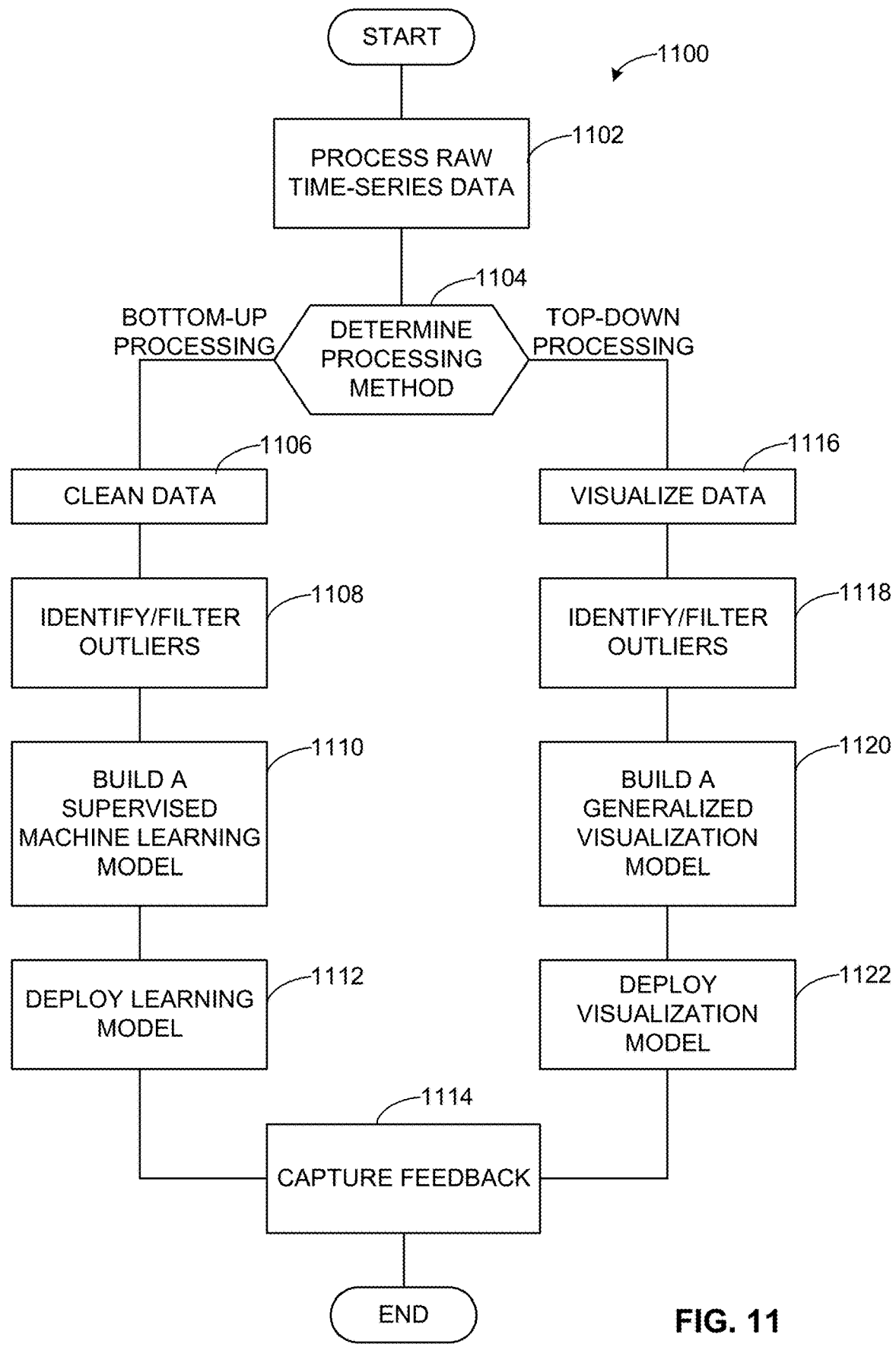
FIGS. 11-13 illustrate flow diagrams of example methods to generate and process synthetic one-dimensional time series data using the example system(s) of FIGS. 2A-3 and/or 8-10.

FIG. 11 is a flow diagram of an example method 1100 to process 1D time series data. At block 1102, raw time series data is processed. For example, 1D waveform data from one or more sensor attached to and/or otherwise monitoring a patient, a medical device, other equipment, a healthcare environment, etc., can be processed by an example processor to identify the data (e.g., type of data, format of data, source of data, etc.) and route the data appropriately.

At block 1104, a processing method to be applied to the data is determined. The processing method can be dynamically determined by the processor based on the type of the data, source of the data, reason for exam, patient status, type of patient, associated healthcare professional, associated healthcare environment, etc. The processing method can be a bottom-up processing method or a top-down processing method, for example. When the processing method is to be a bottom-up processing method, at block 1106, the data is cleaned. For example, the data can be cleaned by the processor to normalize the data with respect to other data and/or a reference/standard value. The data can be cleaned by the processor to interpolate missing data in the time series, for example. The data can be cleaned by the processor to adjust a format of the data, for example. At block 1108, outliers in the data are identified and filtered. For example, outlier data points that fall beyond a boundary, threshold, standard deviation, etc., are filtered (e.g., removed, separated, reduced, etc.) from the data being processed.

At block 1110, a learning model is built using the data. For example, a machine learning model is built (e.g., training and testing a supervised machine learning neural network and/or other learning model, etc.). For example, the model trainer 1030 and/or the model tester 1040 can leverage normalized data, synthetic data, imputed data, etc., to train a machine learning model to correlate output(s) with input(s) and test the accuracy of the model.

At block 1112, the learning model is deployed. For example, the example model deployer 1050 can deploy an executable network model once the model tester 1040 is satisfied with the training and testing. The deployed model can be used to process data, correlate an output (e.g., a graphical representation, identification of an anomaly, identification of a trend, etc.) with input data, convert waveform data to a relative graphical representation, etc.

At block 1114, feedback is captured from use of the deployed model. For example, feedback can be captured from the deployed model itself, feedback can be captured from an application using the model, feedback can be captured from a human user, etc.

When the processing method is to be a top-down processing method, at block 1116, the data is visualized. For example, a processor can be used to process the data to transform the source waveform and/or other 1D time series data into graphical representations. The example processor can normalize and/or otherwise clean the data and transform the 1D data into one or more visual constructs such as blocks/clusters, strips/segments, etc. (see, e.g., FIGS. 5 and 7). The example processor can correlate blocks, strips, etc., based on patient, location/organization/cohort, emergency event, other reference event or marker, etc. At block 1118, outliers in the data are identified and filtered. For example, outlier data points that fall beyond a boundary, threshold, standard deviation, etc., are filtered (e.g., removed, separated, reduced, etc.) from the data being processed by the example processor.

At block 1120, a visualization model is built using the data. For example, the example model trainer 1030 and model tester 1040 build a visualization model (e.g., trains and tests a generalized visualization model, etc.) using data and associated graphical representations to cluster representations for a patient, group patients together in relative alignment around a trigger event (e.g., an emergency condition, an anomaly, a particular physiological value, etc.). The model can thereby learn how and when to group similar or dissimilar graphical representations, highlight anomalies in a visual manner, etc.

At block 1122, the visualization model is deployed. For example, the example model deployer 1050 can deploy an executable visualization model once the model tester 1040 is satisfied with the training and testing. The deployed model can be used to process data, correlate an output (e.g., a graphical representation, identification of an anomaly, identification of a trend, etc.) with input data, convert waveform data to a relative graphical representation, comparatively organize graphical representations according to one or more criteria, etc.

At block 1114, feedback is captured from use of the deployed model. For example, feedback can be captured from the deployed model itself, feedback can be captured from an application using the model, feedback can be captured from a human user, etc.

Figure 12:
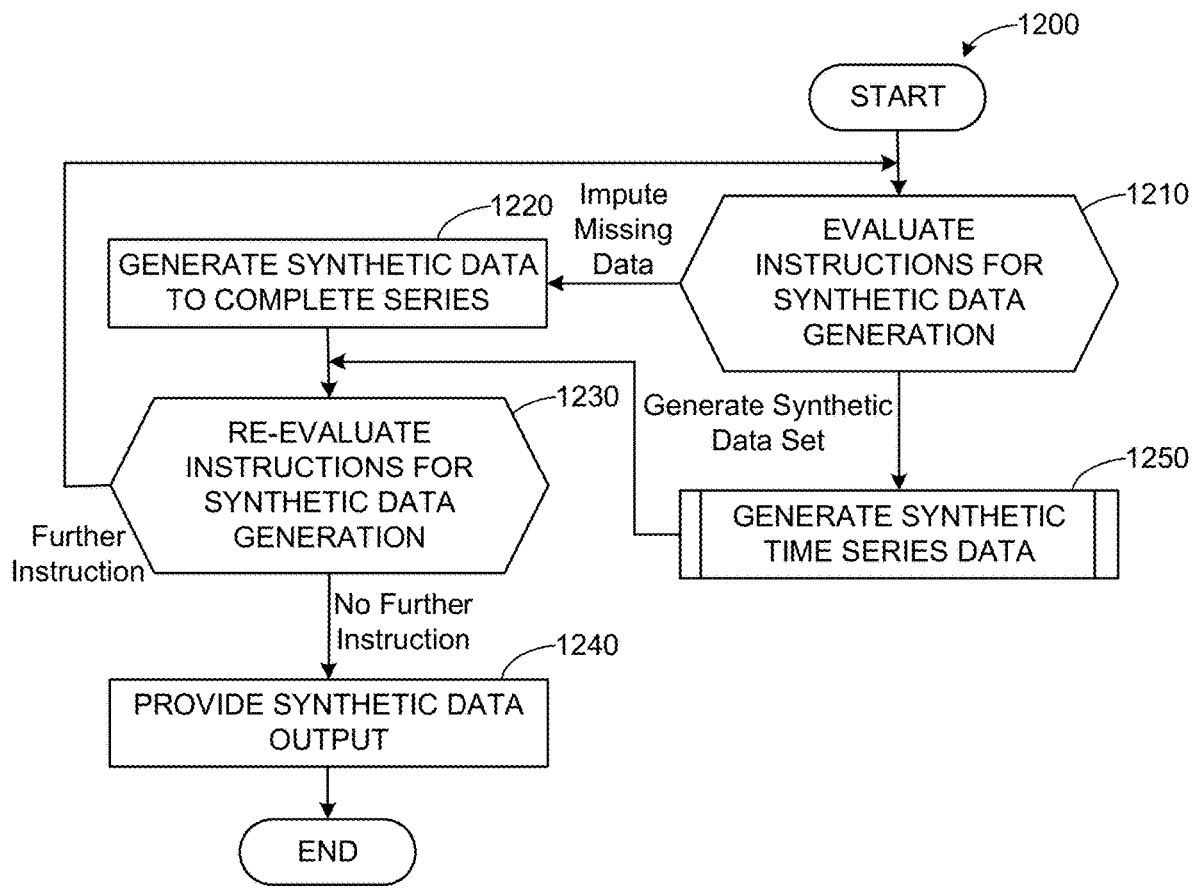

FIG. 12 is a flow diagram of an example method 1200 to generate synthetic 1D time series data. At block 1210, instructions for synthetic data generation are evaluated to determine a type of synthetic data generation. For example, the synthetic data generation can be an imputation of missing data from a waveform. The synthetic data generation can be a generation of a 1D time-series data set, including annotation, for training and/or testing of an AI model, for example. In certain examples, multiple instructions can be included to first impute missing data in a waveform and then use the completed waveform to generate additional synthetic data to form a 1D time-series data set of synthetic or synthetic plus real 1D time series data, such as for training and/or testing of an AI model.

At block 1220, if missing data is to be imputed, then an input waveform is processed to generate synthetic data to complete the waveform. For example, the input waveform is processed (e.g., by the preprocessor(s) 240, 245, the data generator 930, etc.) to determine or "learn" a data distribution of the waveform and additional training data from which the model 270, 275, 300, 800, 930 can generate additional data points including variation from the training data set. The generative model 270, 275, 300, 800 models a distribution that is as similar as possible (e.g., based on a probability distribution, etc.) to the true data distribution of the input data set to impute the missing data.

At block 1230, instructions for synthetic data generation are re-evaluated to determine whether any instructions remain. If one or more additional instructions remain, then control reverts to block 1210 to process such instruction(s). If no further instructions remain to generate synthetic data, then, at block 1240, the synthetic data output is provided to another system, apparatus, device, or processor. For example, the output processor 940 can output a multi-channel signal, combining a plurality of constituent data and annotation channels, etc., for further processing, storage, display, use in training and/or testing an AI model, etc. The output processor can output a single-channel imputed waveform for further processing, storage, display, use in training and/or testing an AI model, etc. For example, the example output processor 940 prepares the correlated data/annotation output for output via the communication interface 910 and use in training an AI model, testing an AI model, etc.

At block 1250, if a training and/or testing data set is to be generated, synthetic 1D time-series data is generated using a first AI network model. For example, synthetic 1D time-series data can be generated using a recurrent GAN model, etc. As described above, the generative model 270, 275, GAN 300, 800, data generator 930, etc., can be used to generate one or more waveforms representing 1D time-series data, etc.

For example, in the example apparatus 900, the 1D data generator 930 includes one or more AI models, such as a t-GAN, other GAN, etc., (e.g., the generative model 270, 275, GAN 300, etc.), to process one-dimensional time series data to generate synthetic (e.g., artificial) data to impute missing data from a waveform (e.g., as shown in the example of FIG. 4, etc.), generate additional synthetic data for a training and/or testing data set (e.g., as shown in the example data set 500 of FIGS. 5-6, etc.), etc. In certain examples, the multi-channel time series data (e.g., each channel corresponding to time series data from a particular source (e.g., sensor, monitor, etc.) and/or of a particular type can include an annotation channel corresponding to an internal and/or external event, label, etc., occurring in conjunction with the time series data. For example, synthetic time series data can be correlated to form annotations that correspond to events occurring with respect to the data (e.g., heart attack, application of anesthesia, shortness of breath, turn on/off anesthesia, ECG r-wave, etc.). The multi-channel time series including 1D data and annotation forms a synthetic data output for training, testing, and/or other development/deployment of AI models, missing data imputation, etc.

Figure 13:
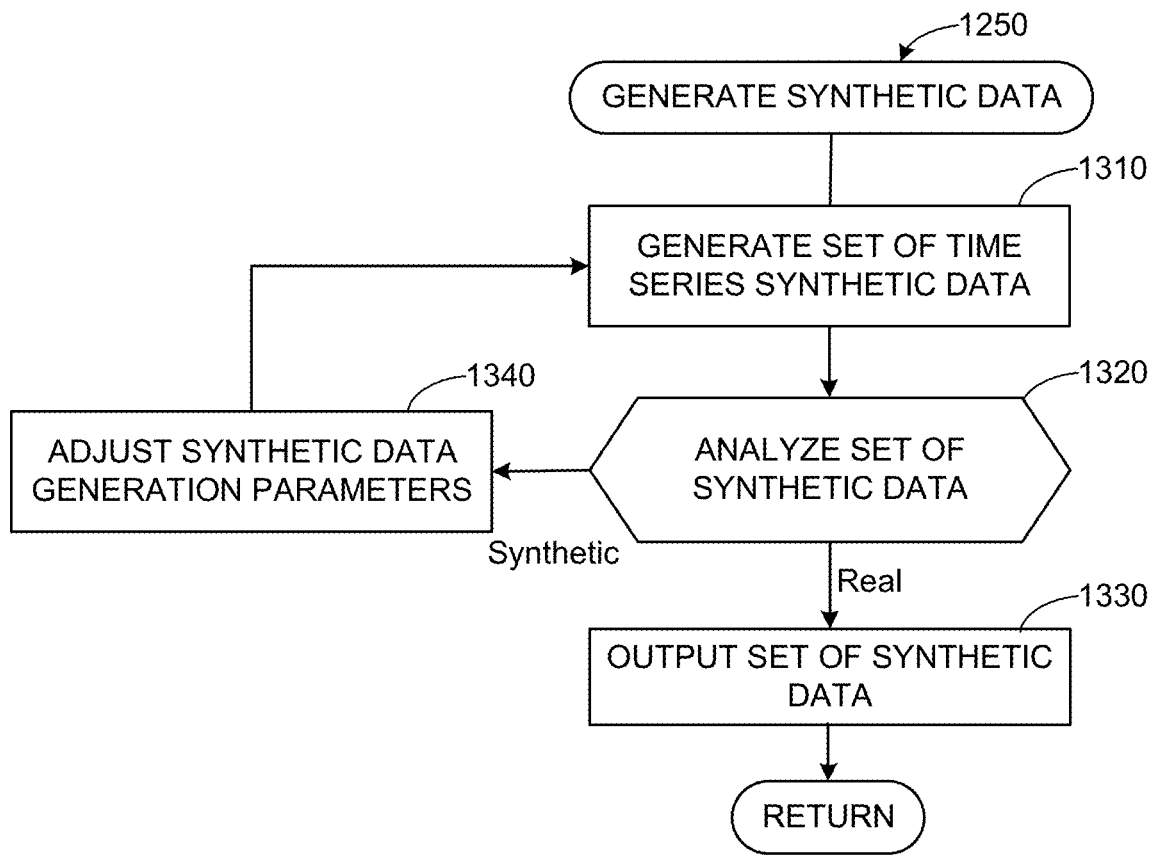

FIG. 13 is a flow diagram of an example method 1300 to generate synthetic time series data (e.g., block 1250 of the example of FIG. 12). At block 1310, a first set of synthetic 1D time series data is generated in one or more channels for each of a plurality of times $t_0, t_1, \ldots t_n$. The data is generated using the apparatus 800, data generator 930, and/or other data generator, for example. The data can be multi-channel data including one or more signal data channels and an annotation/event/label channel for each point in time $t_0, t_1, \ldots t_n$, for example. One or more models such as GAN, LSTM, CNN, RNN, can be used to generate the data channels and annotation channel for each time period $t_0, t_1, \ldots t_n$, for example.

At block 1320, the first set of synthetic data is analyzed or classified to determine its resemblance to actual or "real" captured time series data. For example, the first set of synthetic data can be generated by the example generator 810 of FIG. 8 and analyzed by the example discriminator 820. The discriminator 820 classifies the synthetic data set according to two or more classifications such as real, synthetic, etc. If the first set of synthetic data matches the pattern, value range, and/or other characteristic of the real data (e.g., such that the discriminator 820 cannot tell that the synthetic data is fake), then, at block 1330, the first set of synthetic data is output as a training, testing, and/or other AI model generation/completion data set (and/or combined with other real and/or synthetic data to form such a data set, etc.). For example, if the discriminator 820 thinks that the synthetic data is real data (e.g., classifies the synthetic data set as "real"), then the first synthetic data set can be "finalized" and output for use (e.g., to the model generator 1000, etc.).

However, if the first set of synthetic data does not match the expected/observed/predicted pattern, value range, and/or other characteristic of the real data (e.g., such that the discriminator 820 determines that all or most of the first set of synthetic data is "fake" and classifies the synthetic data set as fake or synthetic), then at block 1340, synthetic data generation parameters are adjusted. For example, synthetic data generation weights, input variable/vector, etc., can be adjusted to cause the generator 810 to generate a different, second set of synthetic data (e.g., including data and annotation channels, only data channel(s), etc.). Control then reverts to block 1310 to generate what is then a second set of synthetic data to be analyzed and output or further refined according to blocks 1310-1340.

As such, a multi-channel time series synthetic data output (with or without associated event or label annotation, etc., such as shown in the example of Table 1 and FIGS. 6A-7, etc.) is generated by one or more AI models, such as a t-GAN, recurrent GAN, other GAN, etc., (e.g., the generative model 270, 275, GAN 300, 800, etc.). This synthetic data output can be provided to a data warehouse, other data storage, and/or directly to a model generator (e.g., model generator 1000, etc.) to be used for testing, training, etc., of an AI model, data imputation, etc.

While example implementations are disclosed and described herein, processes and/or devices disclosed and described herein can be combined, divided, re-arranged, omitted, eliminated and/or implemented in any other way. Further, components disclosed and described herein can be implemented by hardware, machine readable instructions, software, firmware and/or any combination of hardware, machine readable instructions, software and/or firmware. Thus, for example, components disclosed and described herein can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the components is/are hereby expressly defined to include a tangible computer readable storage device or storage disk such as a memory, a digital versatile disk (DVD), a compact disk (CD), a Blu-ray disk, etc. storing the software and/or firmware.

Flowcharts representative of example machine readable instructions for implementing components are disclosed and described herein. In the examples, the machine readable instructions include a program for execution by a processor. The program may be embodied in machine readable instructions stored on a tangible computer readable storage medium such as a CD-ROM, a floppy disk, a hard drive, a digital versatile disk (DVD), a Blu-ray disk, or a memory associated with the processor, but the entire program and/or parts thereof could alternatively be executed by a device other than the processor and/or embodied in firmware or dedicated hardware. Further, although the example program is described with reference to flowchart(s), many other methods of implementing the components disclosed and described herein may alternatively be used. For example, the order of execution of the blocks may be changed, and/or some of the blocks described may be changed, eliminated, or combined. Although the flowchart(s) depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example process(es) can be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process(es) can be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

Figure 14:
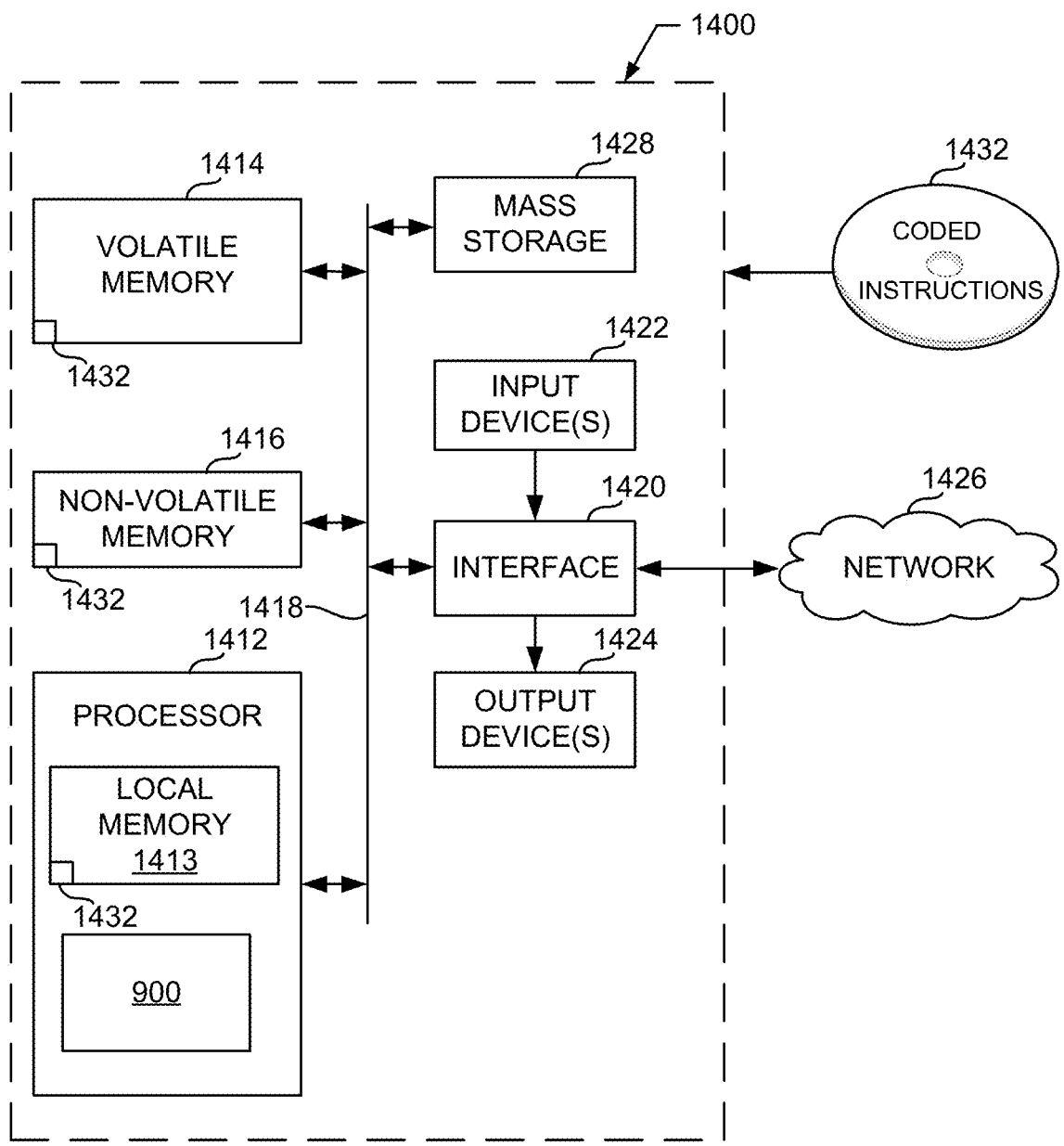
FIG. 14 is a block diagram of an example processor platform capable of executing instructions to implement the example systems and methods disclosed and described herein.

FIG. 14 is a block diagram of an example processor platform 1400 structured to execute the instructions of FIGS. 11-13 to implement, for example the example apparatus 900 and other systems, apparatus, etc., of FIGS. 1-10, such as the apparatus 800, 1000, etc. The processor platform 1400 can be, for example, a server, a personal computer, a workstation, a self-learning machine (e.g., a neural network), a mobile device (e.g., a cell phone, a smart phone, a tablet such as an iPad™), a personal digital assistant (PDA), an Internet appliance, a gaming console, a personal video recorder, a set top box, a headset or other wearable device, or any other type of computing device.

The processor platform 1400 of the illustrated example includes a processor 1412. The processor 1412 of the illustrated example is hardware. For example, the processor 1412 can be implemented by one or more integrated circuits, logic circuits, microprocessors, GPUs, DSPs, or controllers from any desired family or manufacturer. The hardware processor may be a semiconductor based (e.g., silicon based) device. In this example, the processor 1412 implements the example apparatus 900 but can also be used to implement other systems disclosed herein such as systems and/or apparatus 110, 130, 200, 300, 800, 1000, etc.

The processor 1412 of the illustrated example includes a local memory 1413 (e.g., a cache). The processor 1412 of the illustrated example is in communication with a main memory including a volatile memory 1414 and a non-volatile memory 1416 via a bus 1418. The volatile memory 1414 may be implemented by SDRAM, DRAM, RDRAM®, and/or any other type of random access memory device. The non-volatile memory 1416 may be implemented by flash memory and/or any other desired type of memory device. Access to the main memory 1414, 1416 is controlled by a memory controller.

The processor platform 1400 of the illustrated example also includes an interface circuit 1420. The interface circuit 1420 may be implemented by any type of interface standard, such as an Ethernet interface, a USB, a Bluetooth® interface, an NFC interface, and/or a PCI express interface.

In the illustrated example, one or more input devices 1422 are connected to the interface circuit 1420. The input device(s) 1422 permit(s) a user to enter data and/or commands into the processor 1412. The input device(s) can be implemented by, for example, an audio sensor, a microphone, a camera (still or video), a keyboard, a button, a mouse, a touchscreen, a track-pad, a trackball, isopoint, and/or a voice recognition system.

One or more output devices 1424 are also connected to the interface circuit 1420 of the illustrated example. The output devices 1424 can be implemented, for example, by display devices (e.g., an LED, an OLED, an LCD, a CRT display, an IPS display, a touchscreen, etc.), a tactile output device, a printer, and/or speaker. The interface circuit 1420 of the illustrated example, thus, typically includes a graphics driver card, a graphics driver chip, and/or a graphics driver processor.

The interface circuit 1420 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1426. The communication can be via, for example, an Ethernet connection, a DSL connection, a telephone line connection, a coaxial cable system, a satellite system, a line-of-site wireless system, a cellular telephone system, etc.

The processor platform 1400 of the illustrated example also includes one or more mass storage devices 1428 for storing software and/or data. Examples of such mass storage devices 1428 include floppy disk drives, hard drive disks, compact disk drives, Blu-ray disk drives, RAID systems, and DVD drives.

The machine executable instructions 1432 of FIGS. 11-13 may be stored in the mass storage device 1428, in the volatile memory 1414, in the non-volatile memory 1416, and/or on a removable non-transitory computer readable storage medium such as a CD or DVD.

From the foregoing, it will be appreciated that example methods, apparatus and articles of manufacture have been disclosed that enable generation of synthetic, one-dimensional time-series data. The disclosed apparatus, systems, methods, and articles of manufacture enable not only such data to be generated but also generation of annotations corresponding to synthetic events in the synthetic data. As such, certain examples improve the capabilities, efficiency, and effectiveness of processor system, memory, and other associated circuitry by leveraging artificial intelligence models, transformations and expansions of waveform and/or other time-series data, comparative analysis of patient data, etc. In certain examples, missing data from a waveform can be imputed using artificial intelligence models. In certain examples, a series of artificial intelligence models can be combined together to generate and understand synthetic data, correlate synthetic data (alone or in conjunction with real data), generate synthetic event annotations, and combine synthetic event annotations with synthetic data to enable training, testing, and deployment of other artificial intelligence models. The disclosed methods, apparatus and articles of manufacture are accordingly directed to one or more improvement(s) in the functioning of a computer and/or other processor and its associated interface. The apparatus, methods, systems, instructions, and media disclosed herein are not implementable in a human mind and are not able to be manually implemented by a human user.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A synthetic time series data generation apparatus comprising:
    memory storing instructions; and
    at least one processor to execute the instructions to at least:
    a) generate a synthetic data set including i) multi-channel one-dimensional time-series data and ii) associated annotation using a first artificial intelligence network model, the multi-channel one-dimensional time-series data including synthetic waveform signal data, the synthetic data set generated and having a first classification;
    b) analyze the synthetic data set with respect to a real data set using a second artificial intelligence network model to classify the synthetic data set, the real data set collected from at least one patient data source and having a second classification, the second classification different from the first classification at least in that the first classification indicates synthetic data generation by a model and the second classification indicates data captured fora patient;
    c) when the second artificial intelligence network model classifies the synthetic data set as having the first classification, adjust the first artificial intelligence network model, rather than the second artificial intelligence network model, using feedback from the second artificial intelligence network model to tune the first artificial intelligence network model and repeat a)-b), the feedback including the first classification of the synthetic data set by the second artificial intelligence network model, the feedback including a loss function computed between the real data set and the synthetic data set and an error gradient associated with the loss function to adjust at least one parameter of the first artificial intelligence network model; and
    d) when the second artificial intelligence network model classifies the synthetic data set as having the second classification, output the synthetic data set for use in association with the second classification,
    wherein use of the synthetic data set includes to impute synthetic waveform signal data as missing data to complete a captured waveform.

2. The apparatus of claim 1, wherein the first artificial intelligence network model includes a generator of a generative adversarial network model, and wherein the second artificial intelligence network model includes a discriminator of the generative adversarial network model.

3. The apparatus of claim 1, wherein the annotation includes an event associated with the time-series data.

4. The apparatus of claim 3, wherein the event includes at least one of a first event external to a signal represented by the time-series data ora second event internal to the signal represented by the time-series data.

5. The apparatus of claim 1, wherein the processor is to generate the synthetic data set using one or more latent input vectors for a plurality of times.

6. The apparatus of claim 1, wherein the synthetic data set is to be provided to a model generator to at least one of train or test a third artificial intelligence network model.

7. The apparatus of claim 1, wherein the synthetic data set is classified by the at least one processor using a decision aggregator.

8. At least one tangible computer-readable storage medium comprising instructions that, when executed, cause at least one processor to at least:
    a) generate a synthetic data set including i) multi-channel one-dimensional time-series data and ii) associated annotation using a first artificial intelligence network model, the multi-channel one-dimensional time-series data including synthetic waveform signal data, the synthetic data set generated and having a first classification;
    b) analyze the synthetic data set with respect to a real data set using a second artificial intelligence network model to classify the synthetic data set, the real data set collected from at least one patient data source and having a second classification, the second classification different from the first classification at least in that the first classification indicates synthetic data generation by a model and the second classification indicates data captured fora patient;
    c) when the second artificial intelligence network model classifies the synthetic data set as having the first classification, adjust the first artificial intelligence network model, rather than the second artificial intelligence network model, using feedback from the second artificial intelligence network model to tune the first artificial intelligence network model and repeat a)-b), the feedback including the first classification of the synthetic data set by the second artificial intelligence network model, the feedback including a loss function computed between the real data set and the synthetic data set and an error gradient associated with the loss function to adjust at least one parameter of the first artificial intelligence network model; and
    d) when the second artificial intelligence network model classifies the synthetic data set as having the second classification, output the synthetic data set for use in association with the second classification,
wherein use of the synthetic data set includes to impute synthetic waveform signal data as missing data to complete a captured waveform.

9. The at least one tangible computer-readable storage medium of claim 8, wherein the first artificial intelligence network model includes a generator of a generative adversarial network model, and wherein the second artificial intelligence network model includes a discriminator of the generative adversarial network model.

10. The at least one tangible computer-readable storage medium of claim 8, wherein the annotation includes an event associated with the time-series data.

11. The at least one tangible computer-readable storage medium of claim 10, wherein the event includes at least one of a first event external to a signal represented by the time-series data or a second event internal to the signal represented by the time-series data.

12. The at least one tangible computer-readable storage medium of claim 8, wherein the instructions, when executed, cause the processor to generate the synthetic data set using one or more latent input vectors for a plurality of times.

13. The at least one tangible computer-readable storage medium of claim 8, wherein the instructions, when executed, cause the processor to provide the synthetic data set to a model generator to at least one of train or test a third artificial intelligence network model.

14. A computer-implemented method to generate synthetic time series data and associated annotation, the method comprising:
a) generating, using at least one processor, a synthetic data set including i) multi-channel one-dimensional time-series data and ii) associated annotation using a first artificial intelligence network model, the multi-channel one-dimensional time-series data including synthetic waveform signal data, the synthetic data set generated and having a first classification;
b) analyzing, using the at least one processor, the synthetic data set with respect to a real data set using a second artificial intelligence network model to classify the synthetic data set, the real data set collected from at least one patient data source and having a second classification, the second classification different from the first classification at least in that the first classification indicates synthetic data generation by a model and the second classification indicates data capture fora patient;
c) when the second artificial intelligence network model classifies the synthetic data set as having the first classification, adjusting, using the at least one processor, the first artificial intelligence network model, rather than the second artificial intelligence network model, using feedback from the second artificial intelligence network model to tune the first artificial intelligence network model and repeat a)-b), the feedback including the first classification of the synthetic data set by the second artificial intelligence network model, the feedback including a loss function computed between the real data set and the synthetic data set and an error gradient associated with the loss function to adjust at least one parameter of the first artificial intelligence network model; and
d) when the second artificial intelligence network model classifies the synthetic data set as having the second classification, outputting, using the at least one processor, the synthetic data set for use in association with the second classification,
wherein use of the synthetic data set includes to impute synthetic waveform signal data as missing data to complete a captured waveform.

* * * * *

UNITED STATES PATENT AND TRADEMARK OFFICE
CERTIFICATE OF CORRECTION

| | |
|---|---|
| PATENT NO. | : 11,984,201 B2 |
| APPLICATION NO. | : 16/689798 |
| DATED | : May 14, 2024 |
| INVENTOR(S) | : Soni et al. |

It is certified that error appears in the above-identified patent and that said Letters Patent is hereby corrected as shown below:

In the Claims

In Column 26, Claim 4, Line 22, delete "ora" and insert -- or a --.
In Column 26, Claim 8, Line 51, delete "fora" and insert -- for a --.

Signed and Sealed this
Second Day of July, 2024

Katherine Kelly Vidal
*Director of the United States Patent and Trademark Office*